US009283066B2

(12) United States Patent
Hopkins et al.

(10) Patent No.: US 9,283,066 B2
(45) Date of Patent: Mar. 15, 2016

(54) VASCULAR DEVICE FOR EMBOLI, THROMBUS AND FOREIGN BODY REMOVAL AND METHODS OF USE

(71) Applicant: Incept LLC, San Mateo, CA (US)

(72) Inventors: Leo N. Hopkins, Buffalo, NY (US); Farhad Khosravi, San Mateo, CA (US); Amr Salahieh, Campbell, CA (US); Jackson F. Demond, Santa Cruz, CA (US); Jonah Lepak, Santa Cruz, CA (US); Stephen Ramee, New Orleans, LA (US); Jeff A. Krolik, Campbell, CA (US); Richard Renati, San Jose, CA (US)

(73) Assignee: INCEPT LLC, San Mateo, CA (US)

( * ) Notice: Subject to any disclaimer, the term of this patent is extended or adjusted under 35 U.S.C. 154(b) by 0 days.

(21) Appl. No.: 14/108,005

(22) Filed: Dec. 16, 2013

(65) Prior Publication Data

US 2014/0100598 A1  Apr. 10, 2014

Related U.S. Application Data

(63) Continuation of application No. 12/190,319, filed on Aug. 12, 2008, now abandoned, which is a continuation of application No. 10/302,433, filed on Nov. 22, 2002, now Pat. No. 7,410,491, which is a (Continued)

(51) Int. Cl.
*A61M 29/00* (2006.01)
*A61F 2/01* (2006.01)
(Continued)

(52) U.S. Cl.
CPC . *A61F 2/01* (2013.01); *A61F 2/013* (2013.01); *A61B 2017/00287* (2013.01);
(Continued)

(58) Field of Classification Search
CPC ..... A61F 2/01; A61F 2/013; A61F 2230/008; A61F 2230/0008; A61F 2002/018; A61F 2002/011; A61B 2017/2212; A61B 2017/00287; A61M 2025/09183; A61M 2025/1052; A61M 2025/109; A61M 25/0069
USPC ......... 606/108, 110, 113, 114, 127, 194, 198, 606/200
See application file for complete search history.

(56) References Cited

U.S. PATENT DOCUMENTS 3,592,186 A  7/1971  Oster
3,683,904 A  8/1972  Forster
(Continued)

FOREIGN PATENT DOCUMENTS

DE  2821048 C2  7/1980
DE  3417738 A1  11/1985
(Continued)

OTHER PUBLICATIONS

Wholey, Mark H. et al., "PTA and Stents in the Treatment of Extracranial Circulation," The Journal of Invasive Cardiology: vol. 8/Supplement E, Health Management Publications, Inc., 1996, pp. 25E-30E.

(Continued)

*Primary Examiner* — Ashley Fishback
(74) *Attorney, Agent, or Firm* — Seager, Tufte & Wickhem LLP

(57) ABSTRACT

Apparatus and methods are provided for use in filtering emboli from a vessel and/or performing thrombectomy and embolectomy, wherein a vascular device comprises one or more support hoops connected near a distal end of a guide wire, each support hoop having an articulation region, and a blood permeable sac affixed to the support hoop or hoops to form a mouth of the blood permeable sac. The mouth of the sac closes when the apparatus is collapsed for removal to prevent material from escaping from the sac.

13 Claims, 15 Drawing Sheets

Related U.S. Application Data continuation of application No. 09/636,040, filed on Aug. 9, 2000, now Pat. No. 6,544,279, which is a continuation-in-part of application No. 09/470,682, filed on Dec. 23, 1999, now Pat. No. 6,214,026, and a continuation-in-part of application No. 09/470,703, filed on Dec. 23, 1999, now Pat. No. 6,179,861, and a continuation-in-part of application No. 09/470,857, filed on Dec. 23, 1999, now Pat. No. 6,129,739, and a continuation-in-part of application No. 09/430,211, filed on Oct. 29, 1999, now Pat. No. 6,589,263, and a continuation-in-part of application No. 09/364,064, filed on Jul. 30, 1999, now Pat. No. 6,530,939, and a continuation-in-part of application No. 09/470,681, filed on Dec. 23, 1999, now Pat. No. 6,203,561, and a continuation-in-part of application No. 09/611,428, filed on Jul. 7, 2000, now Pat. No. 6,616,679.

(51) Int. Cl.
  *A61B 17/00* (2006.01)
  *A61B 17/221* (2006.01)
  *A61M 25/00* (2006.01)
  *A61M 25/09* (2006.01)
  *A61M 25/10* (2013.01)

(52) U.S. Cl.
  CPC .. *A61B 2017/2212* (2013.01); *A61F 2002/011* (2013.01); *A61F 2002/018* (2013.01); *A61F 2230/008* (2013.01); *A61F 2230/0008* (2013.01); *A61M 25/0069* (2013.01); *A61M 2025/09183* (2013.01); *A61M 2025/109* (2013.01); *A61M 2025/1052* (2013.01)

(56) References Cited

U.S. PATENT DOCUMENTS

| | | |
|---|---|---|
| 3,923,065 A | 12/1975 | Nozick et al. |
| 3,952,747 A | 4/1976 | Kimmell, Jr. |
| 3,996,938 A | 12/1976 | Clark, III |
| 4,046,150 A | 9/1977 | Schwartz et al. |
| 4,318,576 A | 3/1982 | Ford |
| 4,425,908 A | 1/1984 | Simon |
| 4,447,227 A | 5/1984 | Kotsanis |
| 4,580,568 A | 4/1986 | Gianturco et al. |
| 4,590,938 A | 5/1986 | Segura |
| 4,619,246 A | 10/1986 | Molgaard et al. |
| 4,631,052 A | 12/1986 | Kensey |
| 4,643,184 A | 2/1987 | Mobin |
| 4,650,466 A * | 3/1987 | Luther ................ 604/95.04 |
| 4,662,882 A | 5/1987 | Hoffer et al. |
| 4,662,885 A | 5/1987 | Dipisa, Jr. |
| 4,705,517 A | 11/1987 | Dipisa, Jr. |
| 4,706,671 A | 11/1987 | Weinrib et al. |
| 4,723,549 A | 2/1988 | Wholey et al. |
| 4,728,319 A | 3/1988 | Masch et al. |
| 4,733,665 A | 3/1988 | Palmaz |
| 4,790,812 A | 12/1988 | Hawkins et al. |
| 4,790,813 A | 12/1988 | Kensey |
| 4,794,928 A | 1/1989 | Kletschka |
| 4,794,931 A | 1/1989 | Yock et al. |
| 4,800,882 A | 1/1989 | Gianturco et al. |
| 4,807,626 A | 2/1989 | McGirr et al. |
| 4,842,579 A | 6/1989 | Shiber et al. |
| 4,857,045 A | 8/1989 | Rydell et al. |
| 4,857,046 A | 8/1989 | Stevens et al. |
| 4,867,156 A | 9/1989 | Stack |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco et al. |
| 4,921,478 A | 5/1990 | Solano et al. |
| 4,921,484 A | 5/1990 | Hillstead |
| 4,926,858 A | 5/1990 | Gifford et al. |
| 4,950,277 A | 8/1990 | Farr |
| 4,955,895 A | 9/1990 | Sugiyama et al. |
| 4,957,482 A | 9/1990 | Shiber et al. |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg et al. |
| 5,019,088 A | 5/1991 | Farr |
| 5,041,126 A | 8/1991 | Gianturco et al. |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford et al. |
| 5,085,662 A | 2/1992 | Willard et al. |
| 5,087,265 A | 2/1992 | Summers et al. |
| 5,100,423 A | 3/1992 | Fearnot et al. |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,181,920 A | 1/1993 | Mueller et al. |
| 5,190,546 A | 3/1993 | Jervis et al. |
| 5,192,286 A | 3/1993 | Phan |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco et al. |
| 5,314,472 A | 5/1994 | Fontaine et al. |
| 5,318,576 A | 6/1994 | Plassche et al. |
| 5,329,942 A | 7/1994 | Gunther et al. |
| 5,330,484 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer et al. |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |

(56) References Cited

U.S. PATENT DOCUMENTS

| | | |
|---|---|---|
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,662,885 A | 9/1997 | Pollak et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,321 A | 10/1998 | Roubin et al. |
| 5,827,324 A | 10/1998 | Cassell et al. |
| 5,833,644 A | 11/1998 | Zadno et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson et al. |
| 5,908,435 A | 6/1999 | Samuels et al. |
| 5,910,154 A | 6/1999 | Tsugita et al. |
| 5,911,734 A | 6/1999 | Tsugita et al. |
| 5,916,193 A | 6/1999 | Stevens et al. |
| 5,922,020 A | 7/1999 | Klein et al. |
| 5,925,016 A | 7/1999 | Chornenky et al. |
| 5,925,060 A | 7/1999 | Forber et al. |
| 5,925,062 A | 7/1999 | Purdy et al. |
| 5,925,063 A | 7/1999 | Khosravi |
| 5,928,203 A | 7/1999 | Davey et al. |
| 5,928,218 A | 7/1999 | Gelbfish et al. |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard et al. |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,090,097 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,168,604 B1 | 1/2001 | Cano |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,254,633 B1 | 7/2001 | Pinchuk et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,306,163 B1 | 10/2001 | Fitz |
| 6,309,399 B1 | 10/2001 | Barbut et al. |
| 6,319,268 B1 | 11/2001 | Ambrisco et al. |
| 6,336,934 B1 | 1/2002 | Gilson et al. |
| 6,344,049 B1 | 2/2002 | Levinson et al. |
| 6,530,989 B1 | 3/2003 | Anantharaman et al. |
| 6,544,279 B1 | 4/2003 | Hopkins et al. |
| 6,589,263 B1 | 7/2003 | Hopkins et al. |
| 6,592,546 B1 | 7/2003 | Barbut et al. |
| 6,616,679 B1 | 9/2003 | Khosravi et al. |
| 7,410,491 B2 | 8/2008 | Hopkins et al. |
| 2008/0300621 A1 | 12/2008 | Hopkins et al. |

FOREIGN PATENT DOCUMENTS

| | | |
|---|---|---|
| DE | 4030998 A1 | 4/1991 |
| DE | 19916162 A1 | 10/2000 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 A2 | 7/1991 |
| EP | 0472334 A1 | 2/1992 |
| EP | 0472368 A2 | 2/1992 |
| EP | 0533511 A1 | 3/1993 |
| EP | 0655228 A1 | 5/1995 |
| EP | 0686379 A2 | 12/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0852132 A1 | 7/1998 |
| EP | 0934729 A1 | 8/1998 |
| EP | 1127556 A2 | 8/2001 |
| FR | 2580504 A1 | 10/1986 |
| FR | 2643250 A1 | 8/1990 |
| FR | 2666980 A1 | 3/1992 |
| FR | 2694687 A1 | 2/1994 |
| FR | 2768326 A1 | 3/1999 |
| GB | 2020557 A | 11/1979 |

(56) References Cited

FOREIGN PATENT DOCUMENTS

| | | | |
|---|---|---|---|
| JP | 8187294 | | 8/1996 |
| SU | 764684 | T | 9/1980 |
| WO | 9203097 | A1 | 3/1992 |
| WO | 9414389 | A1 | 7/1994 |
| WO | 9424946 | A1 | 11/1994 |
| WO | 9601591 | A1 | 1/1996 |
| WO | 9610375 | A1 | 4/1996 |
| WO | 9619941 | A1 | 7/1996 |
| WO | 9623441 | A1 | 8/1996 |
| WO | 9633677 | A1 | 10/1996 |
| WO | 9717100 | A1 | 5/1997 |
| WO | 9727808 | A1 | 8/1997 |
| WO | 9742879 | A1 | 11/1997 |
| WO | 9802084 | A1 | 1/1998 |
| WO | 9802112 | A1 | 1/1998 |
| WO | 9823322 | A1 | 6/1998 |
| WO | 9833443 | A1 | 8/1998 |
| WO | 9834673 | A1 | 8/1998 |
| WO | 9836786 | A1 | 8/1998 |
| WO | 9838920 | A1 | 9/1998 |
| WO | 9838929 | A1 | 9/1998 |
| WO | 9839046 | A1 | 9/1998 |
| WO | 9839053 | A1 | 9/1998 |
| WO | 9846297 | A1 | 10/1998 |
| WO | 9847447 | A1 | 10/1998 |
| WO | 9849952 | A1 | 11/1998 |
| WO | 9850103 | A1 | 11/1998 |
| WO | 9851237 | A1 | 11/1998 |
| WO | 9855175 | A1 | 12/1998 |
| WO | 9909895 | A1 | 3/1999 |
| WO | 9922673 | A1 | 5/1999 |
| WO | 9923976 | A1 | 5/1999 |
| WO | 9925252 | A1 | 5/1999 |
| WO | 9930766 | A1 | 6/1999 |
| WO | 9940964 | A1 | 8/1999 |
| WO | 9942059 | A2 | 8/1999 |
| WO | 9944510 | A1 | 9/1999 |
| WO | 9944542 | A1 | 9/1999 |
| WO | 9955236 | A1 | 11/1999 |
| WO | 9958068 | A1 | 11/1999 |
| WO | 0007521 | A1 | 2/2000 |
| WO | 0007655 | A1 | 2/2000 |
| WO | 0009054 | A1 | 2/2000 |
| WO | 0016705 | A1 | 3/2000 |
| WO | 0049376 | A1 | 8/2000 |
| WO | 0053120 | A1 | 9/2000 |
| WO | 0067664 | A1 | 11/2000 |
| WO | 0067665 | A1 | 11/2000 |
| WO | 0067666 | A1 | 11/2000 |
| WO | 0067668 | A1 | 11/2000 |
| WO | 0067669 | A1 | 11/2000 |
| WO | 0105462 | A1 | 1/2001 |
| WO | 0108595 | A1 | 2/2001 |
| WO | 0108596 | A1 | 2/2001 |
| WO | 0108742 | A1 | 2/2001 |
| WO | 0108743 | A1 | 2/2001 |
| WO | 0110320 | A1 | 2/2001 |
| WO | 0115629 | A1 | 3/2001 |
| WO | 0121077 | A1 | 3/2001 |
| WO | 0121100 | A1 | 3/2001 |
| WO | 0126726 | A1 | 4/2001 |
| WO | 0135857 | A1 | 5/2001 |
| WO | 0143662 | A1 | 6/2001 |
| WO | 0147579 | A1 | 7/2001 |
| WO | 0149208 | A1 | 7/2001 |
| WO | 0149209 | A1 | 7/2001 |
| WO | 0149215 | A1 | 7/2001 |
| WO | 0149355 | A1 | 7/2001 |
| WO | 0152768 | A1 | 7/2001 |
| WO | 0158382 | A1 | 8/2001 |
| WO | 0160442 | A1 | 8/2001 |
| WO | 0167989 | A1 | 9/2001 |
| WO | 0170326 | A1 | 9/2001 |
| WO | 0172205 | A2 | 10/2001 |
| WO | 0187183 | A1 | 11/2001 |
| WO | 0189413 | A2 | 11/2001 |
| WO | 0191824 | A1 | 12/2001 |

OTHER PUBLICATIONS

Fadall, A. Moneim, "A filtering device for the prevention of particulate embolization during the course of cardiac surgery", Surgery, vol. 64(3), pp. 634-639 (Sep. 1968).
"Atherosclerotic Disease of the Aortic Arch as a Risk Factor of Recurrent Ischemic Stroke," The New England Journal of Medicine, pp. 1216-1221 (May 1996).
"Endovascular Grafts, Stents Drive Interventional Radiology Growth," Cardiovascular Device Update, 2(3):1-12 (Mar. 1996).
Tunick et al., "Protruding Atheromas in the Thoracic Aortic and Systemic Embolization," pp. 423-427 American College of Physicians (1991).
Karalis, et al., "Recognition and Embolic Potential of Intraaortic Atherosclerotic Debris," American College of Cardiology (Jan. 1991).
Cragg, Andrew et al., "A New Percutaneous Vena Cava Filger," AJR, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," J. Endovasc. Surg., 3:182-202 (1996).
Haissaguerre et al., "Spontaneous Initiation of Atrial Fibrillation by Ectopic Beats Originating in the Pulmonary Veins," The New England Journal of Medicine, 339(10):659-666 (Sep. 1988).
Jordan, Jr. et al., "Microemboli Detected by Transcranial Doppler Monitoring . . . ," Cardiovascular Surgery, 7 (1):33-38 (Jan. 1999).
Lesh, "Can Catheter Ablation Cure Atrial Fibrillation?" ACC Current Journal Review, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," American Heart Journal, 125(2 Pt 1):362-366 (Feb. 1993).
Mazur et al., "Directional Atherectomy with the Omnucath.TM.: A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," Rinsho Kyobu Geka, 14(2): English Abstract Only (Apr. 1994).
Onal et al., "Primary Stenting for Complex Atherosclerotic Plaques in Aortic and Iliac Stenoses," Cardiovascular & Interventional Radiology, 21(5):386-392(1998).
Theron et al., "New Triple Coaxial Catheter System for Carotid Angioplasty with Cerebral Protection," American Journal of Neuroradiology, 11:869-874 (1990).
Tunick et al., "Protruding atherosclerotic plaque in the aortic archo f patients with systemic embolization: A new finding seen by transesophageal echocardiography," American Heart Journal 120(3):658-660 (Sep. 1990).
Waksman et al., "Distal Embolization is Common After Directional Atherectomy . . . ," American Heart Journal, 129 (3):430-435 (1995).

* cited by examiner

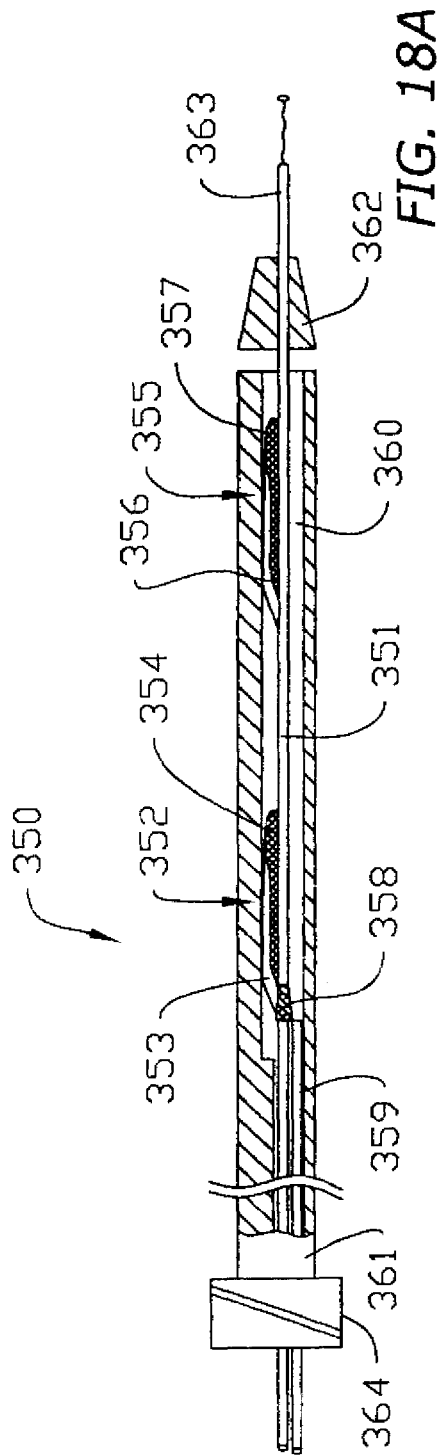
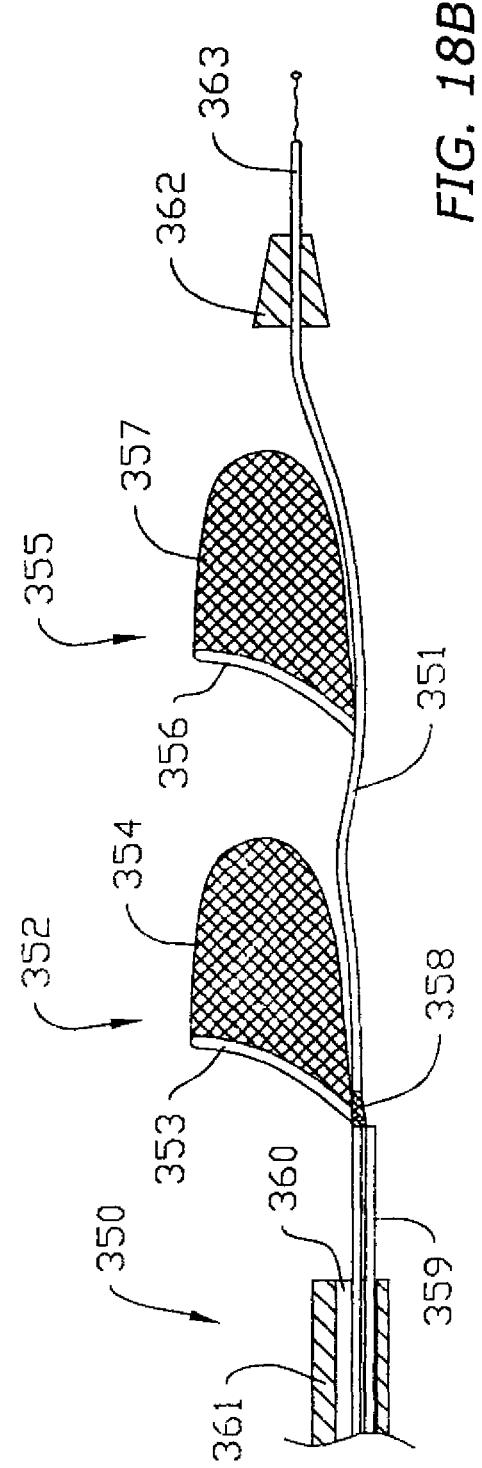
FIG. 18A
FIG. 18B

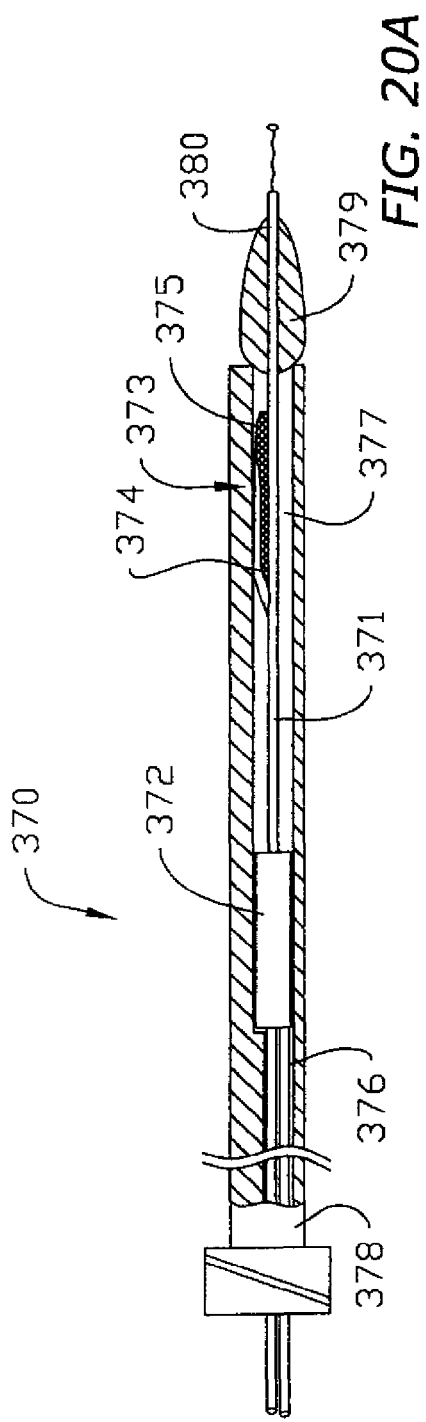
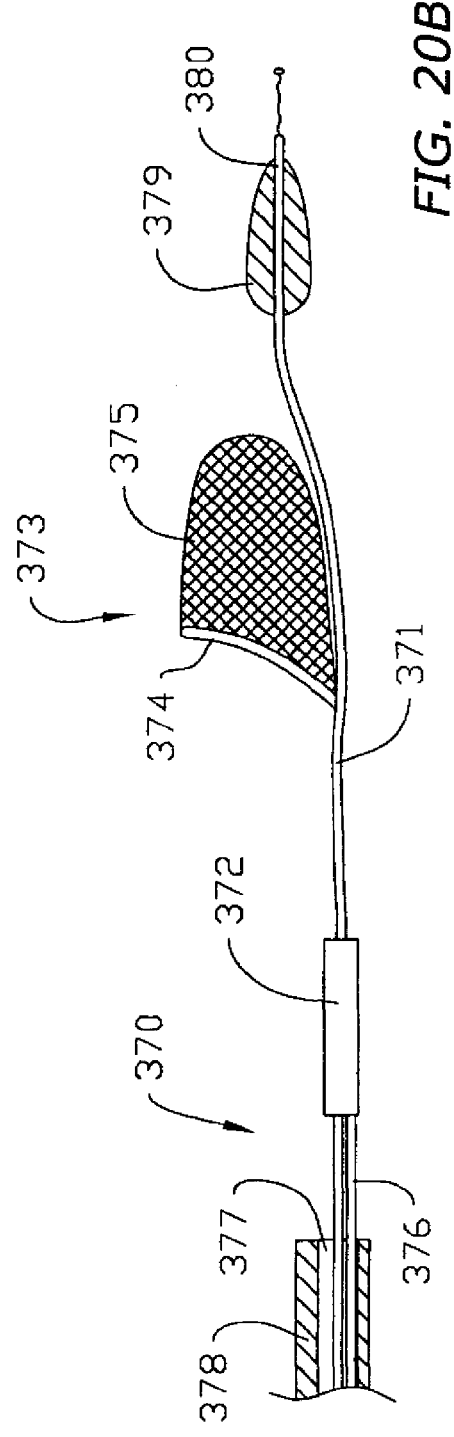
FIG. 20A
FIG. 20B

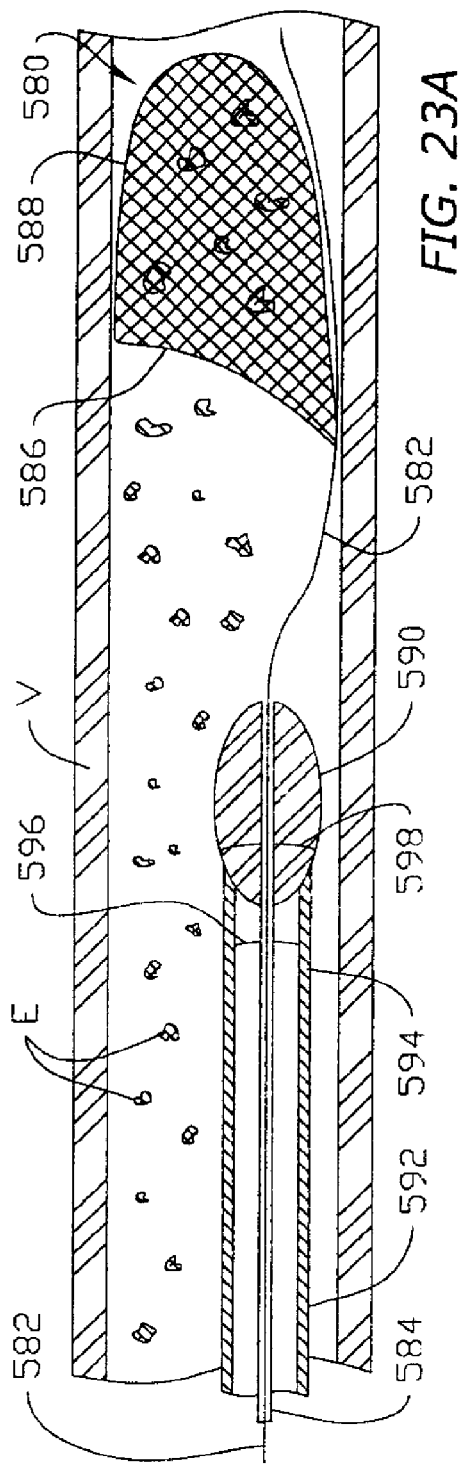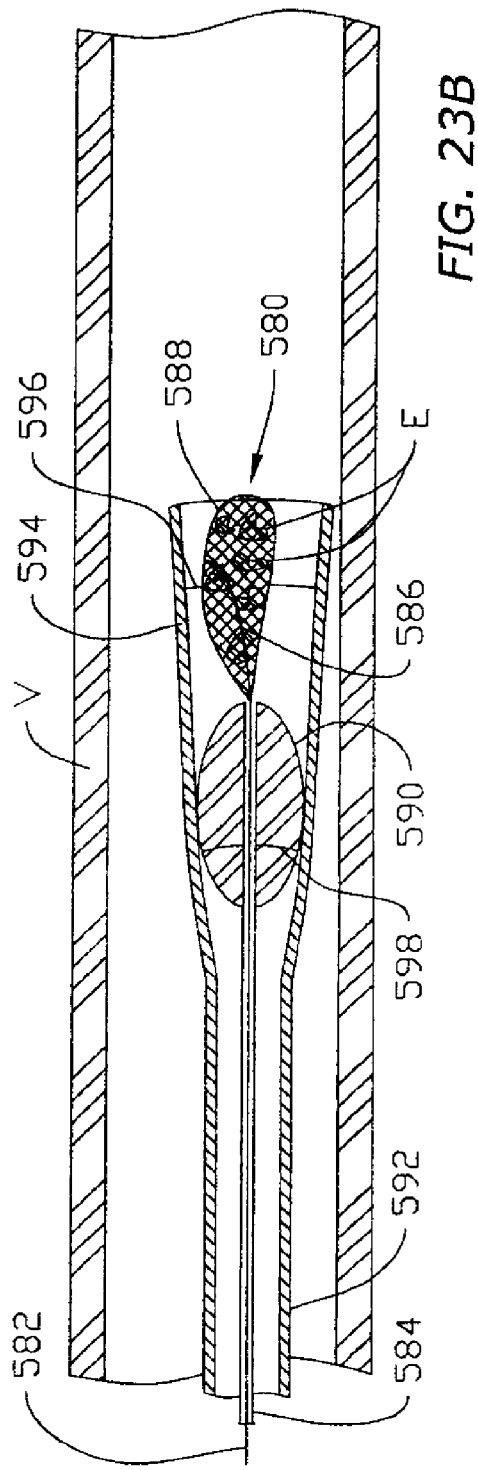

VASCULAR DEVICE FOR EMBOLI, THROMBUS AND FOREIGN BODY REMOVAL AND METHODS OF USE

REFERENCE TO RELATED APPLICATIONS

This application is a continuation of U.S. application Ser. No. 12/190,319, filed Aug. 12, 2008, which is a continuation of U.S. application Ser. No. 10/302,433 filed Nov. 22, 2002, now U.S. Pat. No. 7,410,491, which is a continuation of U.S. patent application Ser. No. 09/636,040, filed on Aug. 9, 2000, now U.S. Pat. No. 6,544,279, which is a continuation-in-part of U.S. patent application Ser. No. 09/470,682 filed Dec. 23, 1999, now U.S. Pat. No. 6,214,026; U.S. Pat. No. 6,544,279 is also a continuation-in-part of U.S. patent application Ser. No. 09/470,703 filed Dec. 23, 1999, now U.S. Pat. No. 6,179,861; U.S. Pat. No. 6,544,279 is also a continuation-in-part of U.S. patent application Ser. No. 09/470,857 filed Dec. 23, 1999, now U.S. Pat. No. 6,129,739; U.S. Pat. No. 6,544,279 is also a continuation-in-part of U.S. patent application Ser. No. 09/430,211 filed Oct. 29, 1999, now U.S. Pat. No. 6,589,263; U.S. Pat. No. 6,544,279 is also a continuation-in-part of U.S. patent application Ser. No. 09/364,064 filed Jul. 30, 1999, now U.S. Pat. No. 6,530,939; U.S. Pat. No. 6,544,279 is also a continuation-in-part of U.S. patent application Ser. No. 09/470,681 filed Dec. 23, 1999, now U.S. Pat. No. 6,203,561; and U.S. Pat. No. 6,544,279 is also a continuation-in-part of U.S. patent application Ser. No. 09/611,428 filed Jul. 7, 2000, now U.S. Pat. No. 6,616,679.

FIELD OF THE INVENTION

The present invention relates to apparatus and methods for filtering or removing matter from within a vascular system. More particularly, the present invention provides a low profile self-expanding vascular device useful for capturing emboli or foreign bodies generated during interventional procedures, and for thrombectomy and embolectomy.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, also involves the introduction of foreign objects into the bloodstream, and also may result in the formation of clots or release of emboli. Such particulate matter, if released into the bloodstream, also may cause infarction or stroke.

Furthermore, interventional procedures may generate foreign bodies that are left within a patient's bloodstream, thereby endangering the life of the patient. Foreign bodies may include, for example, a broken guide wire, pieces of a stent, or pieces of a catheter.

Numerous previously known methods and apparatus have been proposed to reduce complications associated with embolism, release of thrombus, or foreign body material generation. U.S. Pat. No. 5,833,644 to Zadno-Azizi et al., for example, describes the use of a balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as angioplasty balloons or stent delivery systems, are advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage of radially expandable filter systems such as described in the foregoing patents is the relative complexity of the devices, which typically comprise numerous parts. Connecting more than a minimal number of such parts to a guide wire generally increases delivery complications. The ability of the guide wire to negotiate tortuous anatomy is reduced, and the profile of the device in its delivery configuration increases. Consequently, it may be difficult or impossible to use such devices in small diameter vessels, such as are commonly found in the carotid artery and cerebral vasculature. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member, so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, as compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly, and is expected to result in a delivery profile too large to permit use of the device in critical regions of the body, such as the smaller coronary arteries, carotid arteries, and cerebral vasculature.

In view of the foregoing disadvantages of previously known apparatus and methods, it would be desirable to provide a vascular device, e.g., for use as a vascular filter, that overcomes such disadvantages and employs few components.

It would be desirable to provide a reliable and multi-functional delivery system for use with the vascular device.

It would be desirable to provide an integrated vascular device with a thrombectomy element and a vascular filter.

It also would be desirable to provide a vascular device that is capable of being contracted to a small delivery profile, thus permitting use of the device in small vessels.

It further would be desirable to provide a vascular device that is capable of being contracted to a sufficiently small profile that it may be retrieved using the guide wire lumen of previously known treatment devices, and without the need for specialized delivery catheters.

It still further would be desirable to provide a vascular device that reduces the risk of emboli or thrombus removed from the vessel wall escaping from the device when the device is collapsed and removed.

It also would be desirable to provide a vascular device that permits a rapid exchange deployment modality.

SUMMARY OF THE INVENTION

In view of the foregoing, it is an object of the present invention to provide a vascular device that overcomes disadvantages of previously known vascular filters, thrombectomy/embolectomy and foreign body removal devices, and employs few components.

It is an object of the present invention to provide a reliable and multi-functional delivery system for use with the vascular device.

It is an object to provide an integrated vascular device with a thrombectomy element and a vascular filter.

It also is an object of this invention to provide a vascular device that is capable of being contracted to a small delivery profile, thus permitting use of the device in small vessels.

It is a further object to provide a vascular device that is capable of being contracted to a sufficiently small profile that it may be retrieved using the guide wire lumen of previously known treatment devices, and without the need for specialized delivery catheters.

It is another object to provide a vascular device that reduces the risk of emboli or thrombus removed from the vessel wall escaping from the device when the device is collapsed and removed.

It also is an object to provide a vascular device that permits a rapid exchange deployment modality.

These and other objects of the present invention are accomplished by providing a vascular device, suitable for use as a vascular filter or thrombectomy/embolectomy device that comprises a blood permeable sac affixed at its perimeter to a support hoop having an articulation region. The support hoop is attached to a distal region of an elongated member, such as a guide wire, and supports a proximally-oriented mouth of the sac when the device is deployed in a vessel. The device may also comprise a nose cone to facilitate percutaneous introduction, and a delivery sheath having one or more lumens. The lumens may further be configured for a rapid exchange mode of introduction along the guide wire.

In a first embodiment, the support hoop includes one or more reduced-thickness articulation regions that enable the support hoop to be contracted to very small radii of curvature without the problems of increased stiffness and kinking of previously known devices. In an alternative embodiment, the articulation region may comprise a gap in the support hoop bridged by the perimeter of the blood permeable sac.

The support hoop preferably also has a curved profile that prevents the articulation region, when folded, from damaging the wall of the vessel. The curved profile permits the device to effectively contact the walls of the vessel and reduce emboli or thrombus removed from the vessel wall from bypassing the sac. Moreover, the articulation region, when combined with a support hoop having a curved profile, causes the sides of the support hoop to fold inwards towards one-another when the vascular device is collapsed into a sheath for removal. This, in turn, closes the mouth of the sac and reduces the potential for emboli or thrombus to be released from the vascular device during removal.

Advantageously, use of an articulation region permits vascular devices of the present invention to be contracted to very small diameters, thereby enabling the use of delivery catheters having diameters as small as 3 Fr. Moreover, the vascular devices may be retracted within the guide wire lumens of conventional treatment devices, such as angioplasty catheters and stent delivery systems, thereby obviating the need to re-insert a specialized delivery catheter to remove the vascular device. However, a retrieval sheath having a distal region that flares or expands outwardly to receive the emboli-filled sac upon completion of an interventional procedure, and which reduces risk of rupture to the sac, optionally may be provided in accordance with the present invention.

In embodiments suitable for use as embolic filters, the vascular device may include a separate guide wire for introducing treatment devices proximal of the deployed vascular device. Additionally, the vascular device may have a second support hoop attached to the distal end of the sac. During retrieval, multiple hoops ensure that emboli are retained within the sac and prevent the sac from bunching. Where multiple hoops are rotated, they may be arranged such that they rotate independently of the guide wire, thereby reducing risk that the sac wall will become twisted during advancement.

In alternative embodiments, sac bunching is mitigated by tapering the sac and attaching it to one or more support hoops, or to the guide wire. Sac porosity may also be specified to ensure passage of blood cells and capture of emboli, as well as to control a pressure drop across the vascular device. In other embodiments, a delivery sheath is provided that permits a lesion to first be crossed with an unencumbered guide wire prior to passing the vascular device across the lesion. In still further embodiments, several support hoops may be provided at the mouth of a single sac to facilitate opening and closing of the sac.

In thrombectomy applications, a separate thrombectomy element may be provided in addition to the vascular filter. The thrombectomy element may be attached to the elongated member proximal of the vascular filter or may comprise a separate catheter. In a preferred embodiment, the thrombectomy element is similar in construction to the vascular filter and may be refracted independently. Alternatively, the thrombectomy element may be any conventional atherectomy device used in conjunction with the vascular filter and may be advanced and refracted either in conjunction or independently of the vascular filter.

A delivery system in accordance with the present invention, configured for use with the vascular devices described herein, is also provided. The delivery system integrates the functions of a Touhy Borst, a torquer, and a pusher into a single device, thereby facilitating introduction and retrieval of embodiments of the present invention. The torqueing function allows a vascular device to navigate tortuous anatomy. For example, the distal end of a guide wire may be rotated to selectively orient the vascular device in a selected branch of a bifurcated vessel. The Touhy-Borst adapter permits liquid to be introduced or withdrawn through the lumen of the vascular device delivery catheter. The pusher feature of the delivery system allows deployment and refraction of the vascular device from within the delivery catheter.

Methods of using embodiments of the present invention are also provided, including use of novel radiopaque features, and use of a previously known balloon catheter to arrest antegrade flow through a vessel until the vascular device of the present invention is deployed.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 18A and 18B are side-sectional views depicting an integrated vascular device of the present invention suitable for thrombectomy, disposed, respectively, within a delivery sheath and in a deployed state;

FIGS. 20A and 20B are side-sectional views depicting an alternative embodiment of the integrated vascular device of FIG. 18, disposed, respectively, within a delivery sheath and in a deployed state;

FIGS. 23A and 23B are side sectional views depicting a method of using and retrieving the vascular device in conjunction with an alternative embodiment of the specially configured retrieval sheath.

DETAILED DESCRIPTION OF THE INVENTION

Figure 1A:
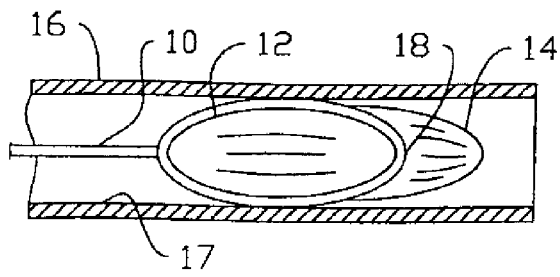
FIGS. 1A and 1B are, respectively, a side-sectional view of a previously known vascular device contracted within a delivery sheath, and an end view of that vascular device deployed in a vessel.
Figure 1B:
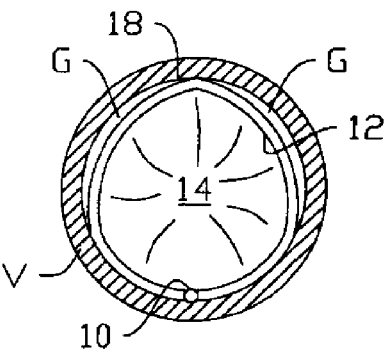

Referring to FIGS. 1A and 1B, some of the disadvantages associated with previously known vascular devices, such as the emboli filters described in the above-mentioned International Publication WO 98/39053, are described. In FIG. 1, the vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of vessel V.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.035" or smaller are used, a hoop of nitinol or multi-strand nitinol cable having a diameter of 0.0055" will form kink 18. Kink 18 in turn may apply relatively high localized pressure and friction against wall 17 of sheath 16, thereby making the vascular filter difficult to deploy. In particular, the kink may impale wall 17 of delivery sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability of the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular device of the present invention solves the above-described disadvantages, providing a vascular device, suitable for use as a vascular filter or thrombectomy/embolectomy device, with a self-expanding support hoop that is sufficiently thick to radially expand and urge a blood permeable sac into engagement with the vessel wall, but which includes an articulation region that overcomes the problems associated with kinking. In particular, the vascular device of the present invention includes a reduced thickness articulation region and a pre-formed curved profile that avoids the difficulties of previously known systems while providing a high degree of efficacy in capturing emboli or thrombus, and ease of deployment and retrieval.

Figure 2A:
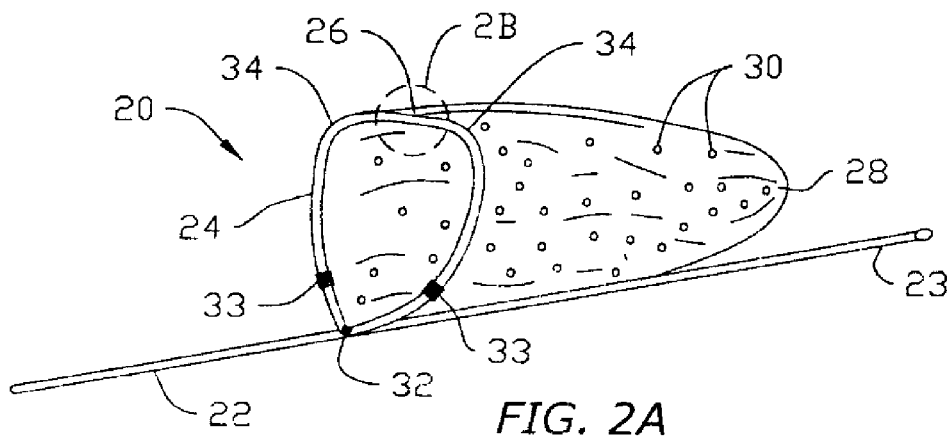
FIGS. 2A and 2B are, respectively, a perspective view of a vascular device constructed in accordance with the principles of the present invention in a deployed state, and a detailed view of the articulation region of the device of FIG. 2A.
Figure 2B:
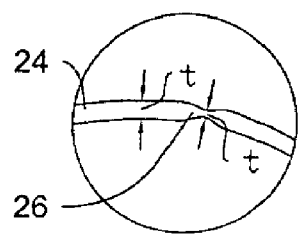

Referring now to FIGS. 2A and 2B, vascular device 20 constructed in accordance with the principles of the present invention, illustratively an embolic filter, comprises guide wire 22, support hoop 24 having articulation region 26, and blood permeable sac 28 affixed to support hoop 24. Sac 28 is coupled to support hoop 24 so that the support hoop 24 forms an opening for the sac. Support hoop 24 preferably is connected to guide wire 22 near distal end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof. The material should be sufficiently thin, such that the sac is non-thrombogenic. Sac 28 includes openings or pores 30 that permit blood cells to pass through the sac substantially unhindered, while capturing any larger emboli, thrombus, or foreign bodies that may be released during a procedure, such as angioplasty or stent placement. In a preferred embodiment, sac 28 has openings or pores 30 in a range of about 20 to 400 microns in diameter, and more preferably, about approximately 80 microns. These pore sizes permit red blood cells (which have a diameter of approximately 5 microns) to easily pass through the sac, while capturing thrombus or emboli.

Pores 30 are preferably formed by a laser drilling process. For example, a thin sheet of the flexible biocompatible material may be thermoformed to create sac 28, for example, by stretching the sheet over a mandrel, by dip forming, or by blow molding. Sac 28 may alternatively be fabricated from an extruded tube of the biocompatible material. A flat metal mask, with tiny holes approximately the size of pores 30, may then be placed in front of the sac. A laser having a beam diameter equal to or greater than the diameter of the material illuminates the mask. The laser beam passes through the holes in the mask and strikes the material, thereby forming pores 30 in sac 28.

Laser drilling may also be accomplished with a laser having a beam diameter approximately the size of pores 30, in which case pores 30 may drilled individually. Sac 28 may alternatively comprise a woven material, for example, formed from the above-mentioned polymers, having a pore diameter determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular device 20, described hereinafter, support hoop 24 folds in half and collapses to fit within a small diameter delivery sheath. When vascular device 20 is in a deployed state, as depicted in FIG. 2A, support hoop 24 resumes its pre-formed shape. Support hoop 24 preferably comprises nitinol wire, although it may also be formed from a multi-strand nitinol cable, a spring tempered stainless steel, or other super-elastic material.

In accordance with the principles of the present invention, support hoop 24 includes one or more reduced-thickness articulation regions 26, and pre-formed curved regions 34. As depicted in FIG. 2B, articulation region 26 includes a region having reduced thickness $t_1$ compared to thickness t of the remainder of support hoop 24. Articulation region 26 and curved regions 34 enable support hoop 24 to fold with a pre-determined shape when vascular device 20 is collapsed to a contracted state for delivery or retrieval.

In FIG. 2B, articulation region 26 is depicted as a localized reduction in the thickness of support hoop 24, as may be achieved, for example, using conventional grinding, chemical etching, or electroless polishing processes. Alternatively, support hoop 24 may be continuously tapered along its circumference, so that articulation region 26 results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In a preferred embodiment of vascular device 20 of the present invention, vascular device 20 easily fits within a delivery sheath having an inner diameter of 0.033", and, more preferably, may be used with a delivery sheath having an inner diameter as small as 0.026". The deployed diameter of support hoop 24 preferably is approximately 7 mm, while guide wire 22 preferably has a diameter of 0.014". The distal end of guide wire 22 also may be tipped with a spring section or coil tip, as is per se known.

Support hoop 24 preferably is constructed of 0.00551" nitinol wire tapered (by a grinding, chemical etching, or electroless polishing process) to 0.0025" at articulation region 26. Specifically, articulation region 26 preferably consists of a length about 0.05" long and having a diameter of 0.0025", coupled on either side to curved regions 34. Each of curved regions 34 includes a length of wire that is tapered from a diameter of 0.055" to a diameter of 0.0025" over a length of about 0.025". Support hoop 24 also may include radiopaque features, such as gold or platinum bands 33, spaced at intervals around the circumference of support hoop 24, or a coil of radiopaque material wrapped around the support hoop, as described hereinafter with respect to FIG. 16, or a gold plated coating.

Figure 3:
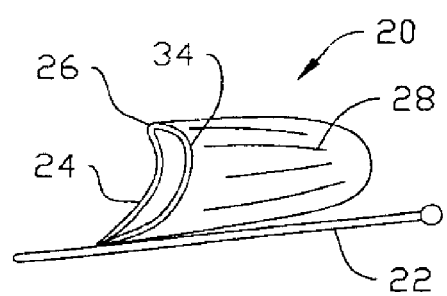
FIG. 3 is a perspective view of the vascular device of FIG. 2 in a folded configuration, prior to removal.
Figure 4:
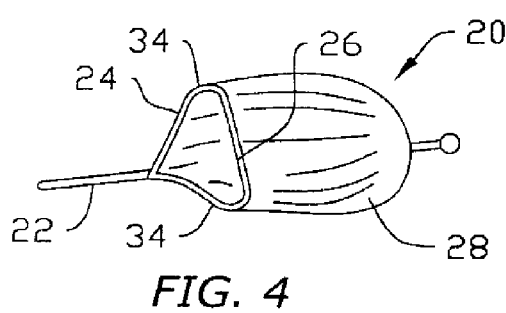
FIG. 4 is a plan view of the vascular device of FIG. 2.

Referring to FIGS. 3 and 4, additional features of vascular device 20 are described. FIG. 3 depicts vascular device 20 of FIG. 2A in a contracted state, while FIG. 4 illustrates a directional change in support hoop 24 preferably caused by the presence of curved regions 34. Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac than would otherwise be possible, without increasing the risk of material escaping from the device when the sac is collapsed for retrieval. Use of a smaller or shallower sac also enables vascular device 20 to be delivered in a smaller delivery sheath, having an inner diameter as small as 0.026" for the preferred embodiment.

Figure 5A:
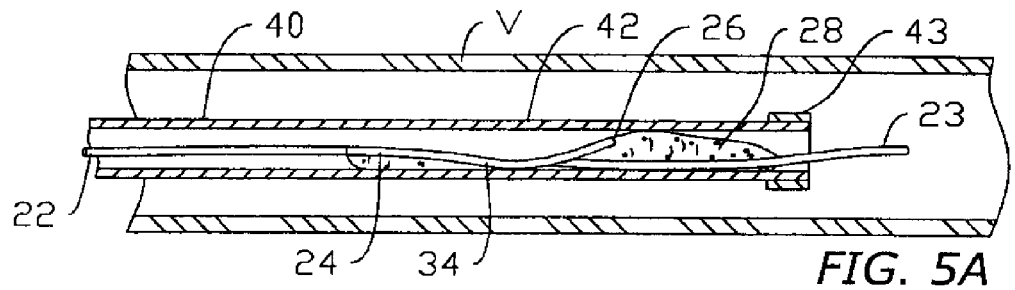
FIGS. 5A-5D are side sectional views depicting a method of deploying, using, and retrieving the vascular device of FIGS. 2-4.

Referring now to FIGS. 5A-5D, methods of using the vascular device of the present invention as a vascular filter are described. In FIG. 5A, guide wire 22 and delivery sheath 40 are manipulated into position within vessel V using well-known percutaneous, techniques. Vascular device 20 of FIG. 2A is disposed in its contracted delivery state within distal end 42 of delivery sheath 40, and delivery sheath 40 is advanced through the vessel using distal end 23 of guide wire 22. Articulation region 26 and curved regions 34 of support hoop 24 enable the sides of the support hoop to fold together and become elongated when drawn within delivery sheath 40. The size of delivery sheath 40 and guide wire 22 have been exaggerated to illustrate structure. In reality, the diameter of delivery sheath 40 is approximately an order of magnitude smaller than the internal diameter of vessel V.

Figure 5B:
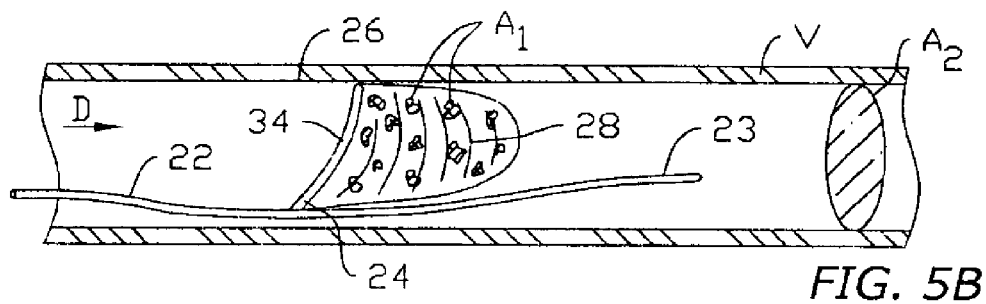

With respect to FIG. 5B, once delivery sheath 40 is disposed at a desired location within a patient's vessel V, such as a coronary artery or carotid artery, as determined, for example, by the position of radiopaque band 43 under a fluoroscope, guide wire 22 is held stationary while delivery sheath 40 is refracted proximally. Alternatively, delivery sheath 40 may be held stationary while guide wire 22 is advanced. In either case, when vascular device 20 is no longer confined within delivery sheath 40, support hoop 24 expands to seal against the walls of vessel V. When in its deployed state, curved regions 34 of support hoop 24 orient articulation region 26 concentrically against the inside wall of the vessel, thus reducing the risk of impaling the vessel wall, as might be expected of the kinked support hoop of FIG. 1B. Blood continues to flow unimpeded through vessel V in direction D.

Figure 5C:
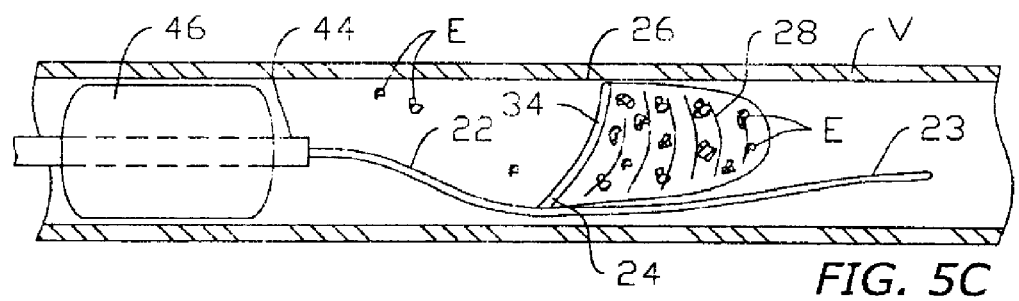

In FIG. 5C, once vascular device 20 is deployed in vessel V, other interventional instruments, such as angioplasty catheters, atherectomy devices, or stent delivery systems may be advanced along guide wire 22 to position such devices at treatment zones located proximally of vascular device 20. For example, in FIG. 5C, angioplasty balloon catheter 44 has been advanced along guide wire 22 to a position proximal of vascular device 20 to trap emboli E, i.e., pieces of plaque dislodged from the walls of vessel V by balloon 46.

Figure 5D:
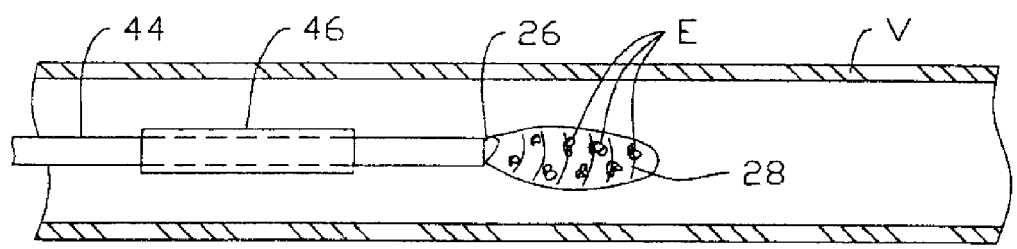

With respect to FIG. 5D, upon completion of the angioplasty procedure using angioplasty balloon catheter 44, guide wire 22 is pulled proximally to cause the sides of support hoop 24 to collapse together to close the mouth of sac 28 (see FIG. 3). Additional proximal retraction of guide wire 22 causes support hoop 24 and sac 28 to enter at least partially within the guide wire lumen of angioplasty catheter 44. As depicted in FIG. 5D, only a portion of support hoop 24, near articulation region 26, and a distal portion of sac 28 extend out of the guide wire lumen of angioplasty catheter 44. Alternatively, vascular device 20 may be fully retracted within the guide wire lumen. Angioplasty catheter 44 then is withdrawn with vascular device 20 and any trapped emboli E.

Advantageously, the compliant design of vascular device 20 permits the device to be contracted to its delivery state within the guide wire lumen of conventional previously known interventional devices. Accordingly, unlike previously known vascular devices, which require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

Vascular device 20 alternatively may be used in performing thrombectomy/embolectomy. In this case, the vascular device is deployed in a vessel at a location distal to a lesion, in the manner depicted in FIGS. 5A and 5B. Once support hoop 24 is deployed into contact with the vessel wall, vascular device 20 may be retracted proximally to scrape along the wall of the vessel, and excise thrombus so that it is captured in sac 28. Delivery sheath 44 may then be re-inserted into the vessel along guide wire 22, and vascular device 20 is retracted and removed from the vessel. Additional thrombectomy embodiments are described hereinbelow with respect to FIGS. 18-20.

As discussed hereinabove, sac 28 is porous so that blood cells may pass through while emboli E are captured. As seen in FIG. 5B, if the sum of the area of all these pores $A_1$ is less than the internal cross-sectional area $A_2$ of vessel V, a pressure drop is expected across the vascular device. This may lead to hemolysis and insufficient downstream flow. If $A_1$ is greater than or equal to $A_2$, the pressure drop is expected to decrease. Proper selection of pore diameter (in the range of 20-400 microns) and pore density ensures that $A_1$ is greater than or equal to $A_2$.

Selection of a larger pore diameter within the provided range may also reduce the pressure drop by decreasing drag as blood passes through sac 28. Drag may further be decreased by providing elliptical pores through the sac that project round relative to bloodflow when sac 28 is deployed. Furthermore, the porosity of sac 28 may be specified such that, if distal pores become occluded with thrombus, emboli, etc., proximal pores remain open to ensure continuous blood flow. It should also be noted that flow through vessel V is substantially unaffected by placement of sac 28 and hoop 24 in the flow path.

Figure 6:
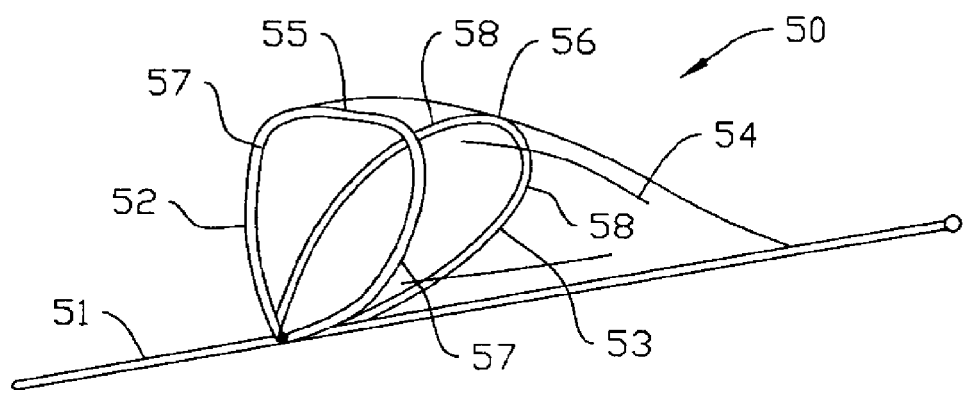
FIG. 6 is a perspective view of an alternative embodiment of a vascular device of the present invention in a deployed state.

Referring now to FIG. 6, an alternative embodiment of the vascular device of the present invention, again illustratively a vascular filter, is described. Vascular device 50 comprises guide wire 51 and support hoops 52 and 53 connected to blood permeable sac 54. As discussed hereinabove, vascular device 50 includes articulation regions 55 and 56 formed at the intersection of opposing curved regions 57 and 58 of support hoops 52 and 53. Sac 54 preferably also is connected to guide wire 51 along its entire length, thereby providing more controlled deployment and removal of vascular device 50. Support hoop 53 serves to stabilize and deploy the distal portion of sac 54. In addition, affixing sac 54 to guide wire 51 may provide a more compact arrangement within a delivery sheath, and prevent bunching of the sac material.

Figure 7A:
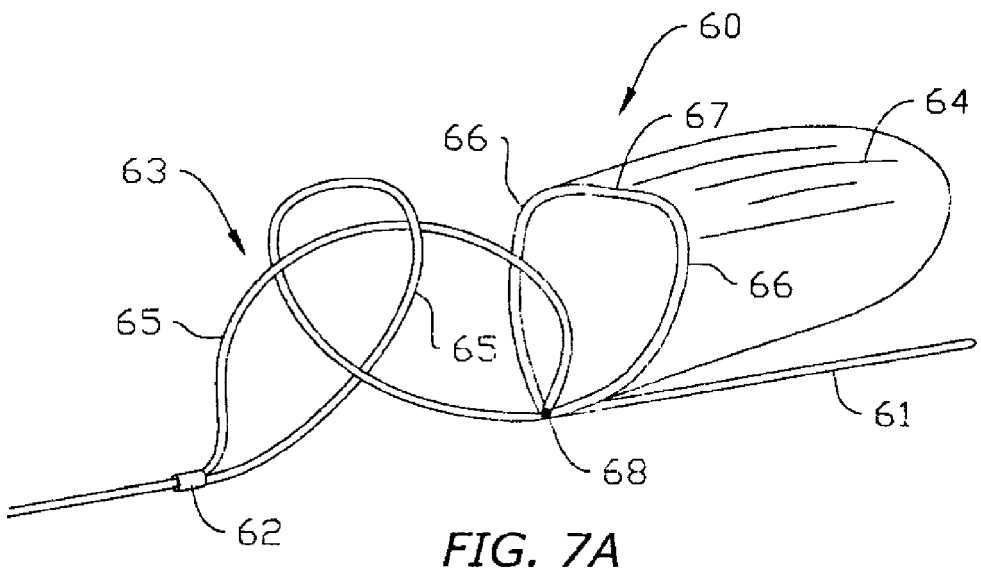
FIGS. 7A and 7B are, respectively, a perspective view and a plan view of a further alternative embodiment of the present invention in a deployed state.
Figure 7B:
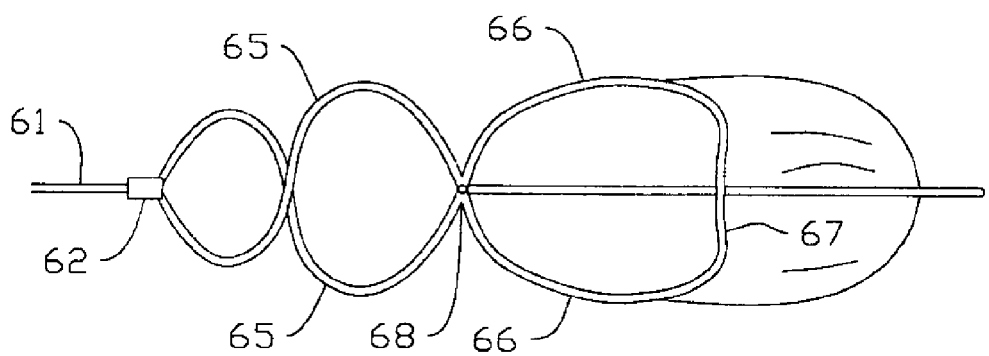

In FIGS. 7A and 7B, a further alternative embodiment of the vascular device of the present invention is described. Vascular device 60, shown in the deployed state, comprises guide wire 61 having multi-turn helical support hoop 63 connected at weld point 62. Blood permeable sac 64 is affixed to the distal-most portion of support hoop 63. Support hoop 63 includes one or more side turns 65 that terminate in curved regions 66, as described hereinabove. Curved regions 66 in turn are joined together by articulation region 67. Preferably, side turns 65 are coupled to one another and to the distal region of guide wire 61, e.g., by a weld bead, at point 68.

In accordance with this aspect of the present invention, vascular device 60 may be contracted to small profile delivery state. When deployed from a delivery catheter, such as delivery sheath 40 of FIG. 5A, side turns 65 expand into contact with the walls of the vessel proximal to the location at which curved regions 66 contact the vessel wall. Side turns 65 serve to stabilize the support hoop 63 and sac 64 when vascular device 60 is deployed within a blood vessel. In addition, side turns 64 are expected to assist in orienting the axis of support hoop 63 and sac 64 in alignment with the longitudinal axis of vessel V. Accordingly, support hoop 63 is expected to reduce the risk of tilting of the vascular device within the vessel, and thus enhance the safety and reliability of the device.

Referring now to FIGS. 8A-8E, several embodiments of a delivery sheath suitable for use with the vascular device of the present invention are described. Each of these embodiments are designed to permit the physician to first pass a guide wire across a lesion before passing the vascular device of the present invention across the lesion. Thus, the risk of generating emboli, during the step of positioning the vascular device of the present invention distal to a lesion, is expected to be reduced.

Figure 8A:
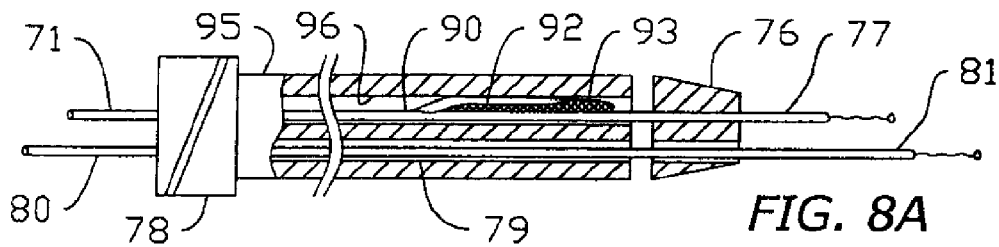
FIGS. 8A-8E are sectional views of a vascular device disposed within alternative embodiments of delivery sheaths of the present invention.

In particular, in FIG. 8A, vascular device 70 of the present invention comprises guide wire 71, support hoop 72 and blood permeable sac 73 folded in a contracted delivery state within lumen 74 of delivery sheath 75. Vascular device 70 is similar in design to vascular device 20 of FIG. 2A, except that device 70 includes nose cone 76 affixed to distal region 77 of guide wire 71. Delivery sheath 75 includes hemostatic fitting 78 at its proximal end and guide wire lumen 79.

In accordance with the methods of the present invention, vascular device 70 and guide wire 80 are used as follows. First, unencumbered guide wire 80 is advanced through a vessel until distal region 81 of the guide wire crosses a lesion. The proximal end of guide wire 80 then is inserted into the distal end of guide wire lumen 79 of delivery sheath 75 using previously known "over the wire" techniques.

Delivery sheath 75 then is advanced over guide wire 80, which is held stationary, until nose cone 76 and a distal portion of the delivery sheath cross the lesion. Once support hoop 72 and sac 73 of vascular device 70 are positioned distal to the lesion, guide wire 80 is withdrawn from the vessel and delivery sheath 75 is retracted proximally, thereby deploying vascular device 70 to its deployed state. As will of course be understood, nose cone 76 remains in the vessel, distal to sac 73, during deployment of the vascular device. Upon completion of use of vascular device 70, delivery sheath 75 may once again be advanced along guide wire 71 and the support hoop and sac retracted within lumen 74 of delivery sheath 75. Alternatively, an interventional device may be advanced over guide wire 71 to perform a medical procedure, and the vascular device may be retrieved within a guide wire lumen of the interventional device, as discussed hereinabove with respect to FIG. 5.

Figure 8B:
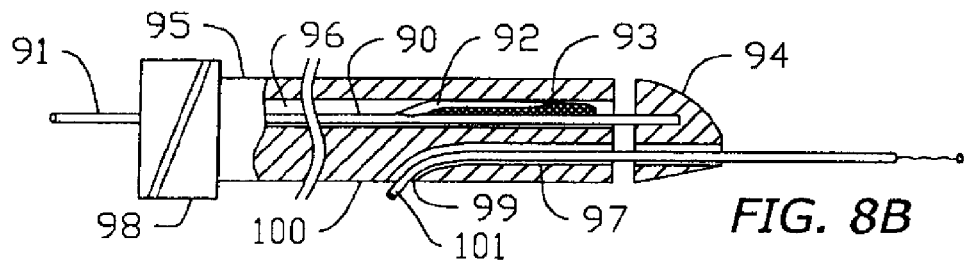

Vascular device 90 of FIG. 8B is similar in construction to that of FIG. 8A, and includes guide wire 91, support hoop 92, blood permeable sac 93 and nose cone 94. Delivery sheath 95 includes lumen 96 housing device 90, guide wire lumen 97, and hemostatic fitting 98. Guide wire lumen 97 opens through skive 99 in lateral wall 100 of delivery sheath 95. Guide wire 101 therefore may be used in accordance with well-known "rapid exchange" techniques, wherein the length of unencumbered guide wire 101 may be significantly shorter than in the case of the "over the wire" arrangement depicted in FIG. 8B. Operation of delivery sheath 95 and vascular device 90 is similar to that described hereinabove with respect to FIG. 8A, except that the proximal end of unencumbered guide wire 101 is passed through the distal end of lumen 97 and passes out through skive 99.

Figure 8C:
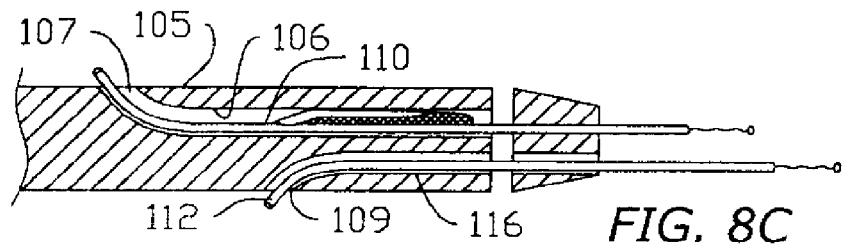

In FIG. 8C, delivery sheath 105 includes lumen 106 that opens through the lateral wall via skive 107, and guide wire lumen 108 that opens through the lateral wall via skive 109. Accordingly, as will be apparent to one of ordinary skill, both vascular device 110 and guide wire 112 may be used as described hereinabove with respect to FIG. 8A and further in accordance with "rapid exchange" techniques.

Figure 8D:
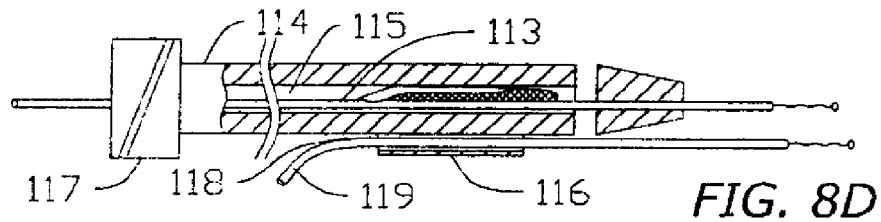

Vascular device 113 of FIG. 8D is similar in construction to those described hereinabove. Delivery sheath 114 includes lumen 115, guide tube 116, and hemostatic fitting 117. Lumen 115 houses device 113 during delivery and retrieval. Guide tube 116 comprises guide wire lumen 118, which is configured to receive unencumbered guide wire 119. In operation, the proximal end of guide wire 119 is passed through guide wire lumen 118 of guide tube 116. Thus, guide wire 119 may be used in accordance with "rapid exchange" techniques described with respect to FIG. 8B and with "over the wire" techniques described with respect to FIG. 8A.

Figure 8E:
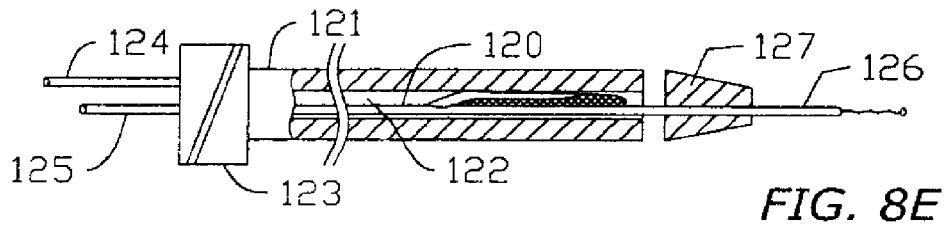

Vascular device 120 of FIG. 8E is also similar to those described hereinabove. Delivery sheath 121 includes lumen 122 and hemostatic fitting 123. Lumen 122 houses device 120. Guide wire 124 is coupled to and terminates at the proximal end of delivery sheath 121. Thus, distal end 126 of guide wire 125 of vascular device 120 is first to cross the lesion. Then, nose cone 127, attached to guide wire 125, and a distal portion of delivery sheath 121 cross the lesion. Guide wire 124 and attached delivery sheath 121 are retracted proximally, thereby deploying vascular device 120 to its deployed state. Device 120 may then be retrieved within sheath 121 or within an interventional device, as discussed hereinabove.

Figure 9:
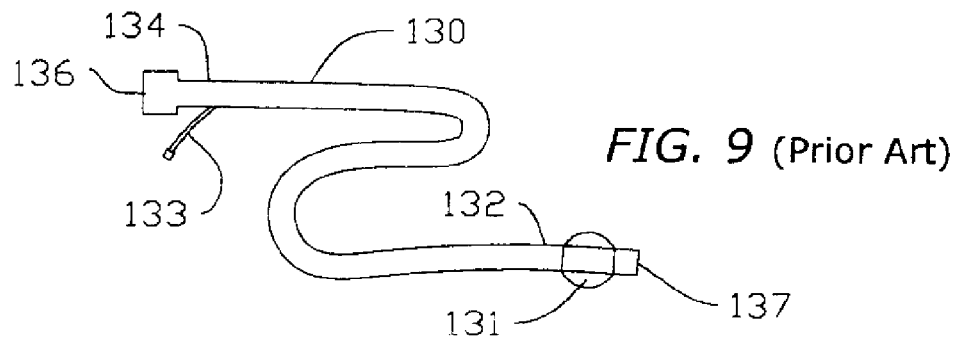
FIG. 9 is a side view of a previously known balloon catheter.

Referring now to FIG. 9, a previously known balloon catheter is described. Catheter 130 is constructed of materials typically used in catheters, such as polyethylene or polyurethane, and includes compliant balloon 131 disposed in distal region 132. Compliant balloon, which may be formed of nylon or latex, is inflated using inflation port 133 at proximal end 134 of the catheter. Catheter 135 also includes hemostatic port 136 and an interior lumen through which a delivery sheath may be advanced to pass out of an opening in distal end 137.

Figure 10A:
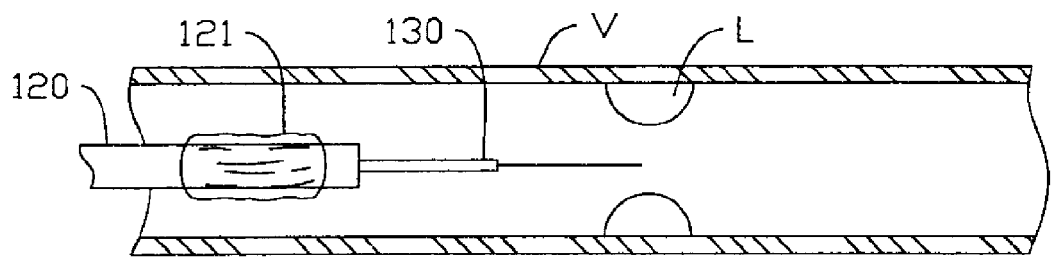
FIGS. 10A-10D are views illustrating the steps of using the balloon catheter of FIG. 9 with the vascular device of FIG. 2.
Figure 10B:
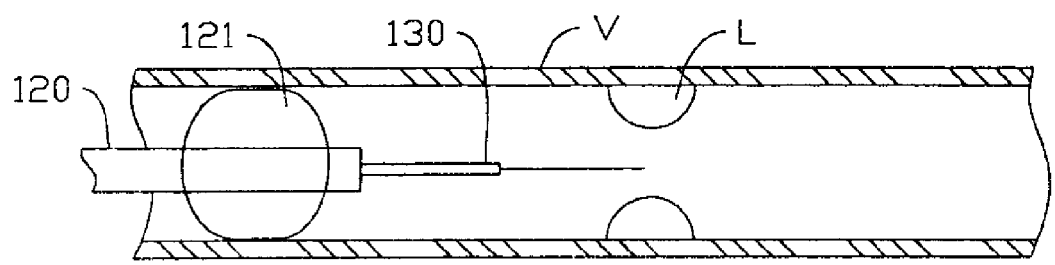
Figure 10C:
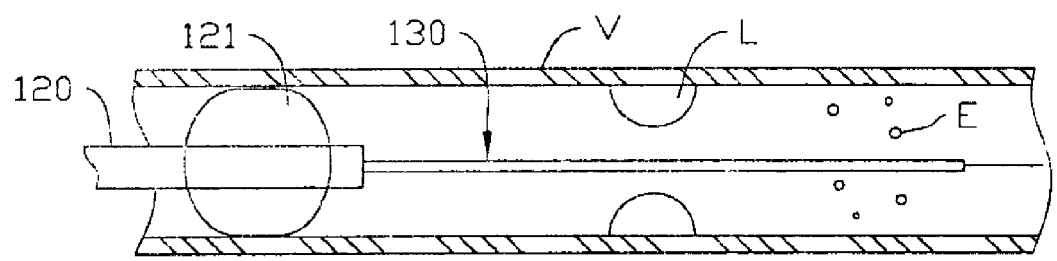

With respect to FIGS. 10A-10C, a method of using catheter 130 of FIG. 9 in conjunction with the vascular device of the present invention is described. In accordance with this aspect of the present invention, antegrade blood flow through a vessel is occluded while a vascular device constructed in accordance with the present invention is advanced across a lesion. Once the vascular device, illustratively a vascular filter, is deployed, the balloon is deflated, thereby permitting antegrade flow to be established. Importantly, because flow through the vessel is stopped prior to deployment of the vascular device, few or no emboli are expected to bypass the filter.

More particularly, with respect to FIG. 10A, catheter 130 is disposed in vessel V at a location proximal to lesion L, with the vascular device of the present invention disposed in its contracted delivery state in delivery sheath 138. In FIG. 10B, balloon 131 is inflated via inflation port 133 to engage the interior wall of vessel V, thereby arresting antegrade flow in the vessel.

As shown in FIG. 10C, delivery sheath 130 then is advanced across lesion L so that the support hoop and sac of the vascular device will be disposed distal to lesion L when deployed. During this step, delivery sheath 138 may generate emboli E as it passes across the lesion. However, because antegrade flow in the vessel is stopped, the emboli will not travel distally in the vessel.

Figure 10D:
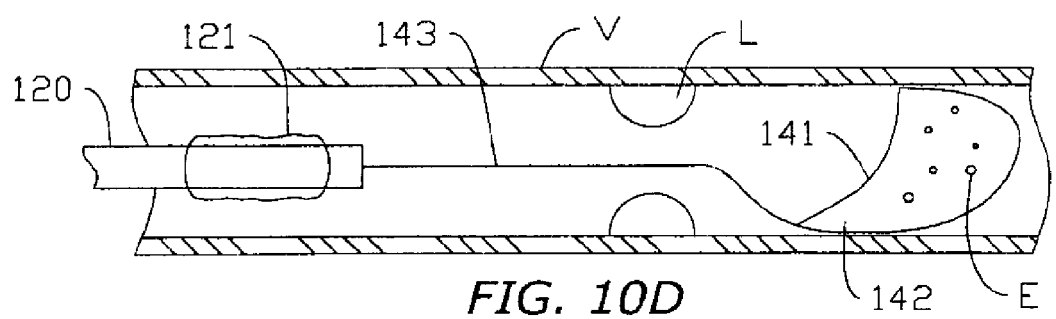

With respect to FIG. 10D, once vascular device 140 is deployed, so that support hoop 141 and sac 142 span vessel V, balloon 131 is deflated. This, in turn, causes antegrade flow to become re-established in vessel V, urging emboli E into sac 142. Catheter 130 then may be withdrawn, and additional treatment devices advanced along guide wire 143 of vascular device 140. Removal of vascular device 140 may be by any of the methods described hereinabove with respect to FIG. 5D.

Figure 11A:
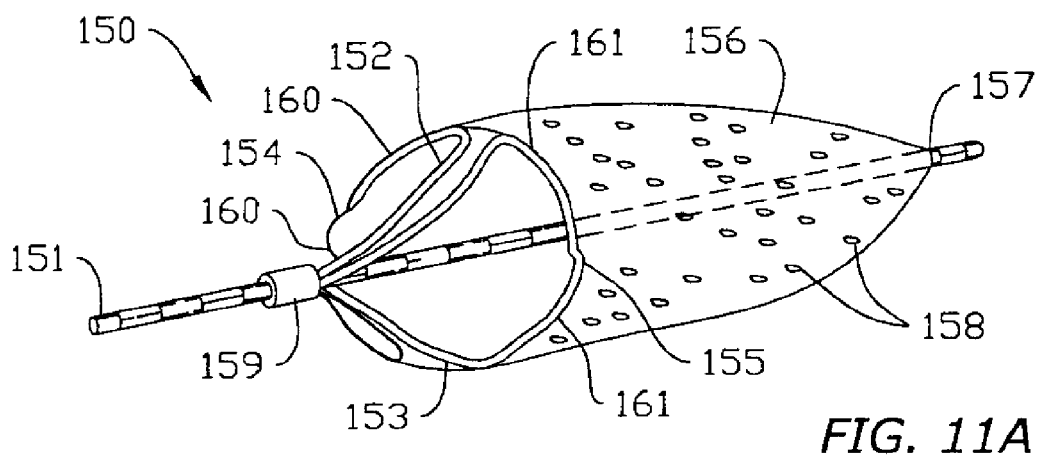
FIGS. 11A-11C are perspective views of further alternative embodiments of vascular devices constructed in accordance with the principles of the present invention.
Figure 11B:
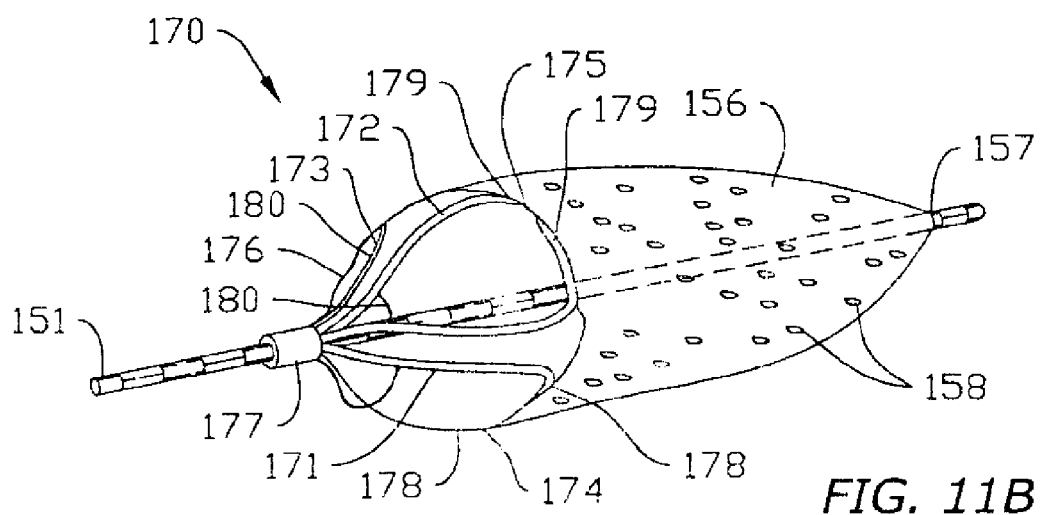
Figure 11C:
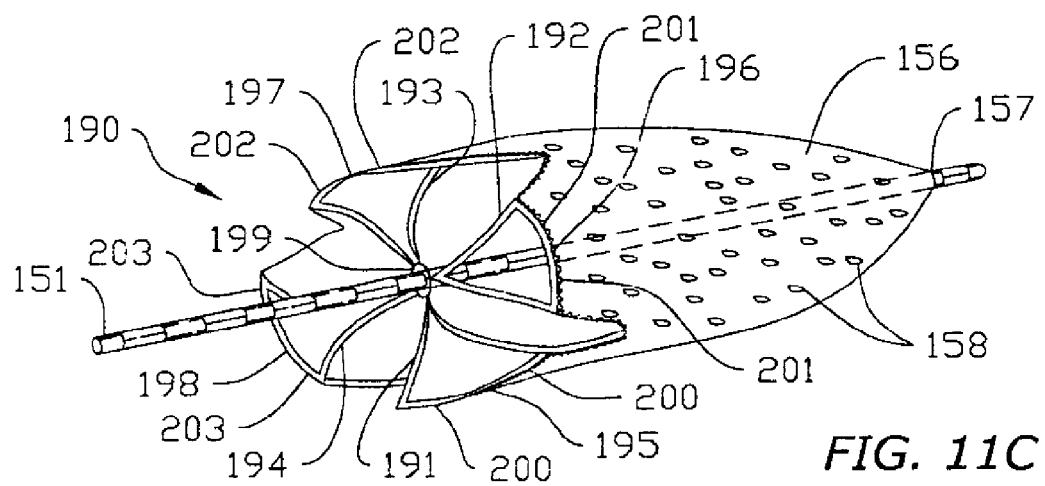

Referring now to FIGS. 11A-11C, still further alternative embodiments of vascular devices constructed in accordance with the present invention are described. Each of the devices of FIGS. 11A-11C, which are shown in the deployed state, includes two or more support hoops to support the blood permeable sac. Each of those support hoops in turn includes an articulation region that permits the sides of the support hoops to collapse inwards to each other as described hereinabove with respect to FIGS. 3 and 4.

Specifically, in FIG. 11A vascular device 150, illustratively an embolic filter, comprises guide wire 151, support hoops 152 and 153 having articulation regions 154 and 155, respectively, and blood permeable sac 156 affixed to support hoops 152 and 153. Sac 156 is coupled to support hoops 152 and 153 so that the support hoops form an opening for the sac. Support hoops 152 and 153 preferably are connected to guide wire 151 near its distal end.

Sac 156 is also attached to the distal end of guide wire 151 at point 157. Sac 156 preferably is constructed of a thin, flexible biocompatible material, as for the embodiments described hereinabove, and includes openings or pores 158 that permit blood cells to pass through the sac substantially unhindered, while capturing any larger material that may be released during a procedure such as angioplasty or stent placement. Pore sizes are selected as described hereinabove with respect to FIG. 2A.

Support hoops 152 and 153 comprise hoops having circular or rectangular cross-sections that are formed of a super-elastic material, such as a nickel-titanium alloy ("nitinol"). During deployment and retrieval of vascular device 150, support hoops 152 and 153 fold in half and collapse to fit within a small diameter delivery sheath. When the delivery sheath is retracted, support hoops 152 and 153 resume their pre-formed shape and deploy the perimeter of sac 156 into contact with the vessel walls. Support hoops 152 and 153 preferably comprise a nitinol wire, but also may be formed from a multi-strand nitinol cable, or other super-elastic material.

In accordance with the principles of the present invention, support hoops 152 and 153 are affixed to guide wire 151 at ring 159 and include reduced-thickness articulation regions 154 and 155, constructed as described hereinabove. More particularly, support hoops 152 and 153 are pre-formed to form structures having curved regions 160 and 161, respectively, so that articulation regions 154 and 155 are disposed in a portion of the support hoop that is approximately concentric with a vessel wall when vascular device 150 is deployed. Articulation regions 154 and 155 and curved regions 160 and 161 thus enable support hoops 152 and 153 to fold with a pre-determined shape when vascular device 150 is collapsed to a contracted state for delivery or retrieval.

In a preferred embodiment of vascular device 150 of the present invention, vascular device 150 easily fits within a delivery sheath having an inner diameter of 0.033", and more preferably, may be used with a delivery sheath having an inner diameter as small as 0.026". The deployed diameter of vascular device 150 preferably is approximately 7 mm.

Compared to vascular device 20 of FIGS. 2-4, vascular device 150 of FIG. 11A employs two support hoops instead of one and provides central location of guide wire 151 and attachment of blood permeable sac 156 to the distal end of the guide wire. These differences may provide more controlled deployment and removal of vascular device 150. In addition, affixing sac 156 to guide wire 151 may provide a more compact arrangement within a delivery sheath, and prevent bunching of the sac material.

Referring now to FIG. 11B, another alternative embodiment of the vascular device of the present invention, again illustratively a vascular filter, is described. Vascular device 170 is similar in construction to vascular device 150, except that vascular device 170 employs three support hoops instead of two. Device 170 comprises guide wire 151 and support hoops 171, 172 and 173 connected to blood permeable sac 156.

As discussed hereinabove, vascular device 170 includes articulation regions 174, 175 and 176 formed at the intersection of opposing curved regions 178, 179 and 180 of support hoops 171, 172 and 173. Support hoops 171, 172 and 173 preferably are connected to the distal end of guide wire 151 at ring 177. Sac 156 preferably also is connected to guide wire 151 at point 157. Vascular device 170 is expected to provide similar advantages to those contemplated for vascular device 150.

With reference to FIG. 11C, yet another alternative embodiment of the vascular device of the present invention, again illustratively a vascular filter, is described. Vascular device 190 is similar in construction to vascular devices 150 and 170, except that vascular device 190 employs four articulated support hoops. Device 190 comprises guide wire 151 and support hoops 191, 192, 193 and 194 connected to blood permeable sac 156, with articulation regions 195, 196, 197 and 198 formed at the intersection of opposing curved regions 200, 201, 202 and 203 of the respective support hoops 191-194. Support hoops 191-194 are preferably connected to the distal end of guide wire 151 at ring 199.

Alternative embodiments of vascular devices of the present invention have been described with one to four support hoops. As will be apparent to one of ordinary skill in the art of interventional device design, any number of support hoops may be used with minor modifications to the designs described hereinabove.

Figure 12:
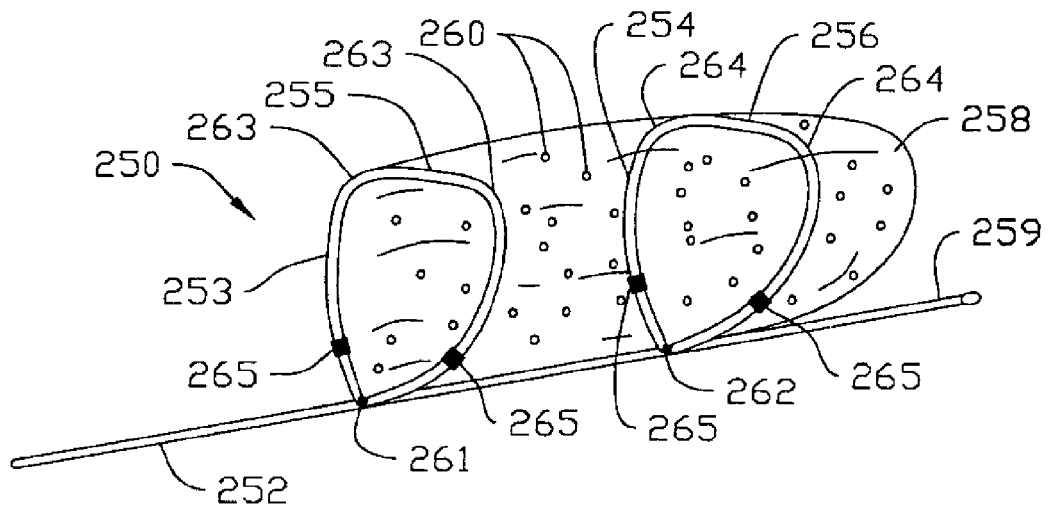
FIG. 12 is a perspective view of an alternative embodiment of the vascular device of the present invention with two support hoops, shown in a deployed state.

Referring now to FIGS. 12-15, further alternative embodiments of the vascular device of the present invention are described. In FIG. 12, vascular device 250, illustratively an embolic filter, comprises guide wire 252, support hoops 253 and 254 having articulation regions 255 and 256, respectively, and blood permeable sac 258 affixed to support hoops 253 and 254. Sac 258 is coupled to support hoop 253 at its proximal end so that the support hoop forms an opening for the sac. Sac 258 is coupled to support hoop 254 at its distal end to prevent emboli from spilling from sac 258 during retrieval. Support hoops 253 and 254 preferably are connected to guide wire 252 near distal end 259 of the guide wire. Sac 258 has openings or pores 260 that permit red blood cells to easily pass through the sac.

During deployment and retrieval of vascular device 250, support hoops 253 and 254 expand and collapse as discussed hereinabove with respect to support hoop 24 of FIG. 2. Support hoops 253 and 254 are attached to guide wire 252 at attachment points 261 and 262, respectively, and further comprise curved regions 263 and 264, respectively. Support hoops 253 and 254 may include radiopaque features, such as gold or platinum bands 265, spaced at intervals around the circumference of the hoops.

Applicant expects that vascular device 250 may further reduce the risk that captured emboli could spill during retrieval, and also may provide a better seal against the artery.

Figure 13:
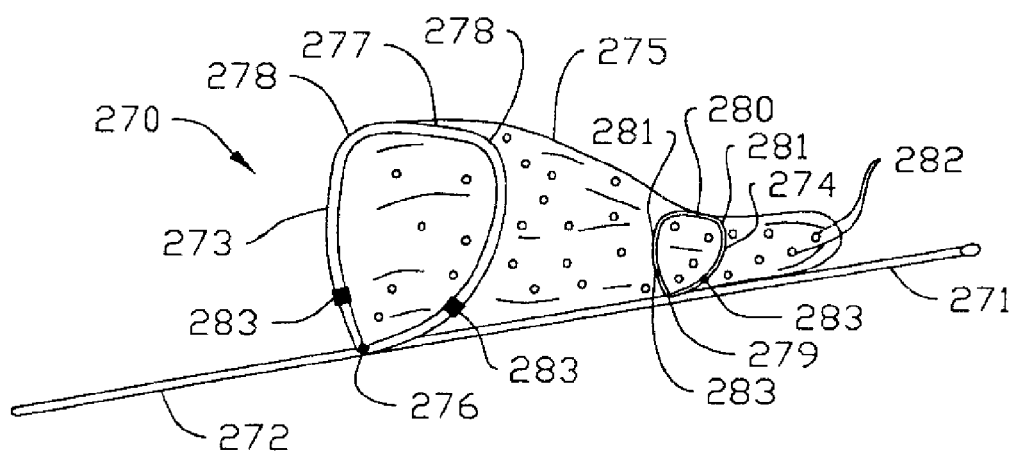
FIG. 13 is a perspective view of an alternative embodiment of the vascular device of FIG. 12 with a smaller distal support hoop.

With reference to FIG. 13, an alternative embodiment of vascular device 250 that prevents bunching is disclosed that may provide even further benefits. Vascular device 270 comprises guide wire 272 on which proximal support hoop 273 and distal support hoop 274 are disposed. The proximal and distal portions of blood permeable sac 275 are affixed to support hoops 273 and 274, respectively. Proximal support hoop 273 is attached to distal end 271 of guide wire 272 at attachment point 276 and includes articulation region 277 and curved regions 278. Likewise, distal support hoop 274 is attached to guide wire 272 at attachment point 279 and includes articulation region 280 and curved regions 281. Sac 275 includes blood permeable pores 282. Hoops 273 and 274 may include radiopaque features, such as gold or platinum bands 283, spaced at intervals around the circumference of the hoops.

Proximal support hoop 273 is significantly larger in circumference than distal hoop 274. Proximal hoop 273 seals against the artery walls and defines the diameter of the mouth of sac 275. Smaller distal hoop 274 prevents emboli from spilling from sac 275 when retrieving device 270. It also allows the diameter of sac 275 to decrease along its length. This taper in sac 275 is expected to reduce the risk that sac 275 will bunch when the sac is retrieved. Sac 275 may further by attached to guide wire 272.

Applicant has determined that where multiple support hoops are employed, as in the embodiments of FIGS. 12 and 13, twisting of the guide wire during deployment may prevent the sac of the vascular device from properly sealing against the vessel wall. For example, if guide wire 252 in the embodiment of FIG. 12 is rotated after distal hoop 254 has been deployed, but before proximal hoop 253 has been deployed, proximal hoop 253 may deploy at an angle with respect to distal hoop 254. This, in turn, may constrict, or all together close, the opening of sac 258, thereby rendering the vascular device ineffective.

Figure 14:
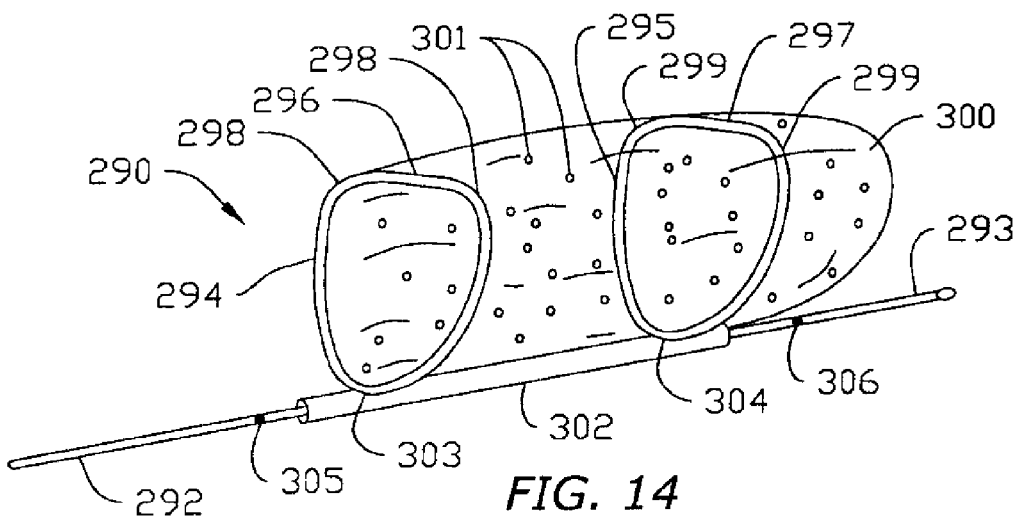
FIG. 14 is a perspective view of a still further alternative embodiment of the vascular device of FIG. 12 that allows the vascular device to independently rotate with respect to the guide wire.

FIG. 14 discloses a vascular device in accordance with the present invention that overcomes problems associated with twisting of the guide wire during deployment. Vascular device 290 comprises guide wire 292 with distal end 293, and support hoops 294 and 295. Support hoops 294 and 295 further comprise articulation regions 296 and 297, respectively, and curved regions 298 and 299, respectively. The proximal and distal portions of blood permeable sac 300 are attached to support hoops 294 and 295, respectively. Sac 300 includes pores 301. Support hoops 294 and 295 are attached to sheath 302 at attachment points 303 and 304, respectively. Sheath 302 preferably comprises a flexible, 0.001" thick tube made of a biocompatible material, such as polyamide or polytetraethylene. Guide wire 292 passes through the lumen of sheath 302. Sheath 302 is able to rotate with respect to guide wire 292 but is translationally restrained by stops 305 and 306, for example, solder beads.

By attaching support hoops 294 and 295 to sheath 302, rotational problems are mitigated. Sheath 302 only transmits translational motion of guide wire 292 to support hoops 294 and 295. Thus, twisting moments applied to wire 292 will not affect the performance of vascular device 290. Sac 300 may also be attached to sheath 302.

Figure 15:
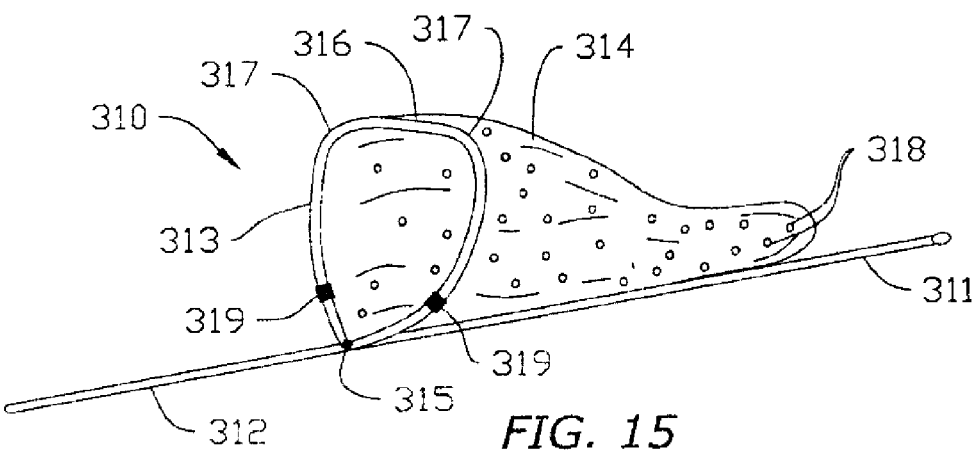
FIG. 15 is a perspective view of an alternative embodiment of the present invention with a tapered blood permeable sac, shown in a deployed state.

With reference to FIG. 15, a further alternative embodiment of the vascular device of the present invention is disclosed that also prevents bunching. Vascular device 310 comprises guide wire 312 on which support hoop 313 is disposed. Tapered blood permeable sac 314 is affixed to support hoop 313. Hoop 313 is attached to distal end 311 of guide wire 312 at attachment point 315 and includes articulation region 316 and curved regions 317. Tapered sac 314 includes blood permeable pores 318. Hoop 313 may include radiopaque features, such as gold or platinum bands 319, spaced at intervals around the circumference of the hoop.

As with vascular device 270 of FIG. 13, the diameter of tapered sac 314 decreases along its length to reduce the risk of bunching when the sac is retrieved. Tapering also reduces the amount of material that must fit within the lumen of a delivery sheath, and thereby allows a delivery sheath of smaller profile to be used. Furthermore, tapering the blood permeable sac reduces the risk that the sac will snag on a stent during retrieval.

Because vascular device 310 lacks the distal support hoop of the embodiments of FIGS. 12 and 13, there is a reduced risk of problems associated with twisting. In a preferred embodiment, the diameter at the distal end of tapered sac 314 is less than the internal diameter of the retrieval sheath with which the apparatus is used. Tapered sac 314 may optionally be attached to guide wire 312, for example, to further mitigate bunching.

Figure 16:
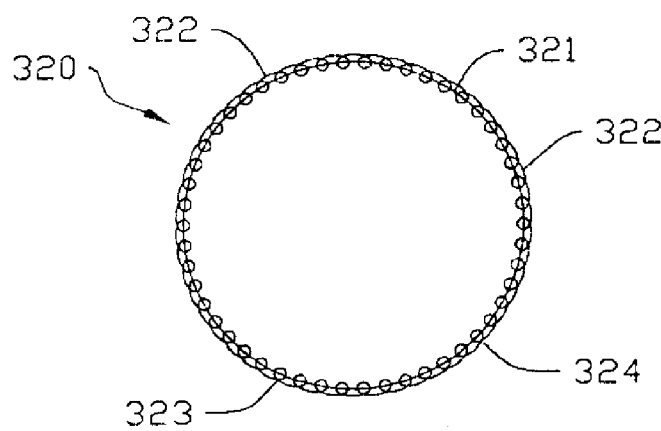
FIG. 16 is a perspective view of a radiopaque support hoop constructed in accordance with one aspect of the present invention.

Referring now to FIG. 16, a support hoop including a radiopaque feature is disclosed. Support hoop 320, illustratively shown in the deployed state, comprises articulation region 321, curved regions 322, attachment point 323, and wound radiopaque wire 324. In the preferred embodiment, wire 324 is platinum and is either round or a strip approximately 0.001" in diameter. Wire 324 is wrapped around hoop 320 all along its circumference.

One method of making a vascular device radiopaque is to electroplate platinum or gold onto the device. However, electroplating can be complex and expensive, and may cause manufacturing difficulties. Because the hoop must change shape during deployment and retrieval, increased thickness or flaking of plated gold are undesirable characteristics and may promote failure of the support hoop. By wrapping wire 324, hoop 320 maintains its strength and flexibility. Radiopaque wire 324 may be used in conjunction with any of the vascular devices discussed herein. Radiopaque wire 324 may further be used with a wide variety of other vascular filter devices, as are known in the art.

Figure 17A:
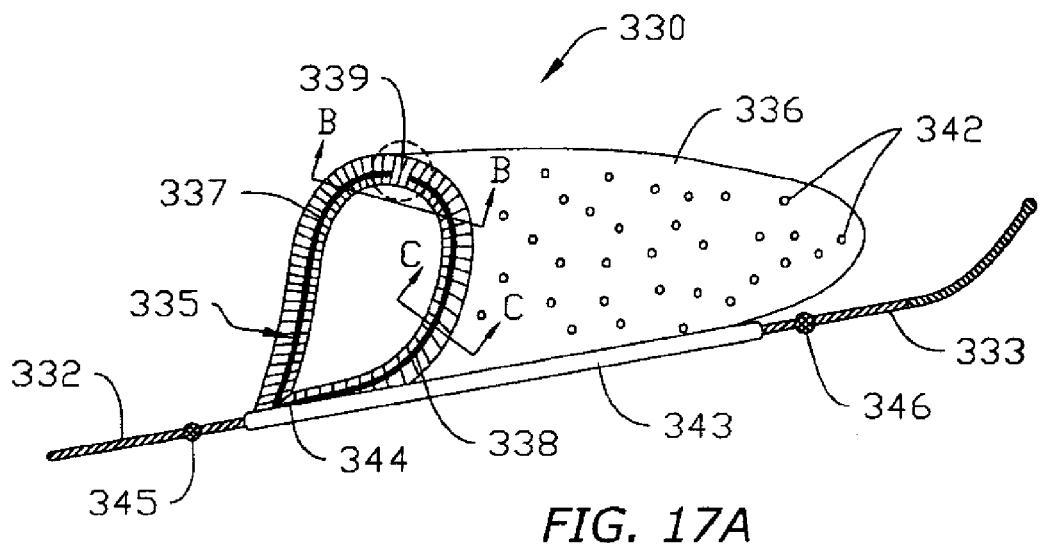
FIGS. 17A-17C illustrate another alternative embodiment of the vascular device of the present invention in which the articulation region comprises a gap in the support hoop bridged by the perimeter of the blood permeable sac.
Figure 17B:
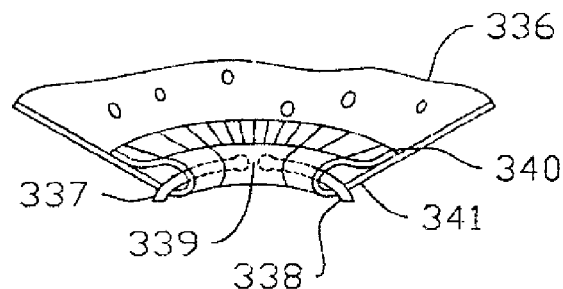
Figure 17C:
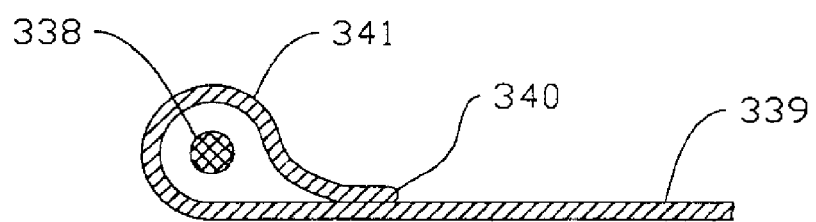

Referring now to FIGS. 17A-17C, another alternative embodiment of the vascular device of the present invention is described. As illustrated in FIG. 17A, vascular device 330 comprises guide wire 332 with distal region 333, wishbone sup port hoop 335, and blood permeable sac 336. Wishbone hoop 335 comprises spines 337 and 338 separated by a gap that serves as articulation region 339. Articulation region 339 is shown in greater detail in FIG. 17B, which corresponds to the area circled in FIG. 17A taken along section line B-B. Blood permeable sac 336 is wrapped around and attached to itself all along its perimeter, creating hem bond 340 and lumen 341. Sac 336 includes pores 347. Lumen 341 is configured to receive spines 337 and 338 and bridge the gap between them. FIG. 17C is a sectional view taken along line C-C of FIG. 17A, showing hem bond 340 and lumen 341 with spine 338 passing there through.

Referring again to FIG. 17A, wishbone support hoop 335 is attached to sheath 343 at attachment point 344. Sheath 343 is similar to sheath 302 of the embodiment of FIG. 14, and preferably comprises a flexible, 0.001" thick tube made of a biocompatible material, such as polyamide or polytetraethylene. Distal end 333 of guide wire 332 passes through the lumen of sheath 343. Sheath 343 may rotate with respect to guide wire 332 but is translationally restrained by stops 345 and 346, for example, solder beads. Sheath 343 mitigates rotational problems by only transmitting translational motion of guide wire 332 to wishbone hoop 335. Twisting moments applied to wire 332 do not affect the performance of vascular device 330.

The wishbone design of support hoop 335 advantageously enables a wider variety of materials to be used to fabricate the support hoop. Articulation region 339 allows vascular device 330 to deploy and contract in a manner similar to that described above for alternative embodiments. Deployment and refraction of wishbone hoop 335 induces minimal deformation of spines 337 and 338, thereby permitting use of materials such as spring steel. As will of course be apparent, the support hoop of the embodiment of FIGS. 17A-17C may advantageously be incorporated in any of the foregoing embodiments.

Referring now to FIGS. 18A and 18B, an integrated vascular device suitable for thrombectomy is described. The integrated device comprises a thrombectomy element and a vascular filter. In a preferred embodiment, the thrombectomy element is similar in construction to vascular filter 20 described above and is connected to the guide wire proximal of the vascular filter. Alternatively, the thrombectomy element may be disposed on a separate catheter. The thrombectomy element may be retracted independently of the vascular filter.

In FIG. 18, integrated vascular device 350 comprises guide wire 351, thrombectomy element 352 including support hoop 353 and blood permeable sac 354, and vascular filter element 355 including support hoop 356 and blood permeable sac 357. Filter hoop 356 is attached to guide wire 351 while thrombectomy hoop 353 is attached to ring 358. Ring 358 is attached to pull wire 359 and has a bore through which guide wire 351 passes. Ring 358 therefore acts as a linear bearing and allows thrombectomy hoop 353 to be moved by pull wire 359 independently of guide wire 351. Alternatively, thrombectomy element 352 may omit sac 354 and simply comprise a wire hoop; in this case severed thrombus is captured by vascular filter 355.

In FIG. 18A, support hoops 353 and 356 and blood permeable sacs 354 and 356 are contracted to a delivery state within lumen 360 of delivery sheath 361. Delivery sheath 361 includes nose cone 362 affixed to distal region 363 of guide wire 351. In FIG. 18B, integrated vascular device 350 is shown deployed in a vessel. As illustrated in FIG. 18B, vascular filter 355 expands to engage the perimeter of the vessel and prevent thrombus from bypassing the blood permeable sac, while thrombectomy element 352 engages the vessel wall proximal of vascular filter 355. As described hereinbelow, proximal movement of thrombectomy device 352 scrapes thrombus from the wall of the vessel when pull wire 359 pulls ring 358 and support hoop 353 proximally.

Figure 19A:
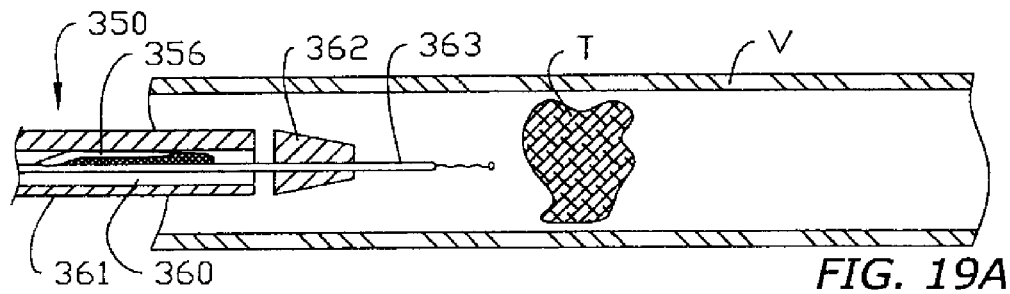
FIGS. 19A-19E are side-sectional views depicting a method of deploying, using, and retrieving the integrated vascular device of FIG. 18.

Referring now to FIGS. 19A-19E, an illustrative method of using the integrated vascular device of the present invention for thrombectomy is described. In FIG. 19A, guide wire 351 is manipulated into position proximal to thrombus T within vessel V using well-known percutaneous techniques. Vascular device 350 of FIGS. 18A and 18B is disposed in its contracted delivery state within the distal end of delivery sheath 361 and the delivery sheath is advanced through the vessel using distal end 363 of guide wire 351. The sides of support hoops 353 and 356 are folded together and become elongated when drawn within delivery sheath 361, as described with respect to vascular device 20 of FIGS. 2-4.

Figure 19B:
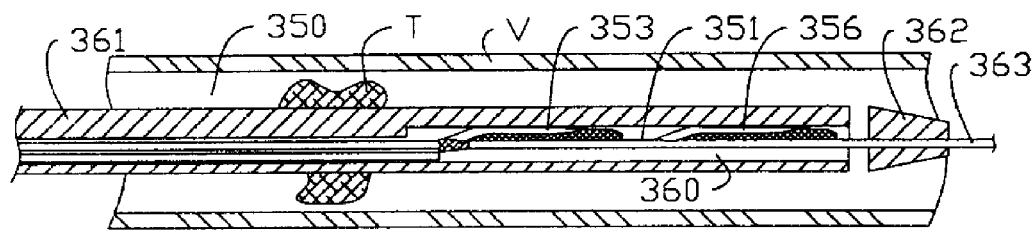

With respect to FIG. 19B, once delivery sheath 361 is disposed at the desired location proximal to thrombus T within a patient's vessel V, such as a coronary artery or carotid artery, based on the position of, for example, radiopaque bands under a fluoroscope, integrated vascular device 350 is advanced through thrombus T. Distal end 363 of guide wire 351 is advanced through the lesion, then nose cone 362 gradually increases the diameter of the void within thrombus T so that the remainder of delivery sheath 361 can be advanced far enough that thrombectomy element 352 (still within delivery sheath 361) is located distal to thrombus T.

Figure 19C:
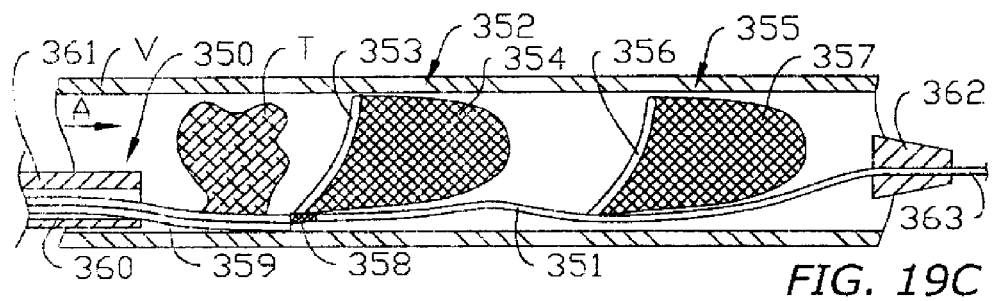

With integrated vascular device 350 in position, guide wire 351 is held stationary while delivery sheath 361 is retracted proximally, as seen in FIG. 19C. Alternatively, delivery sheath 361 may be held stationary while guide wire 351 is advanced. In either case, when vascular device 350 is no longer confined within delivery sheath 361, support hoops 353 and 356 expand to seal against the walls of the vessel V and deploy blood permeable sacs 354 and 357, respectively. Blood continues to flow through vessel V in direction A, impeded only by thrombus T.

Figure 19D:
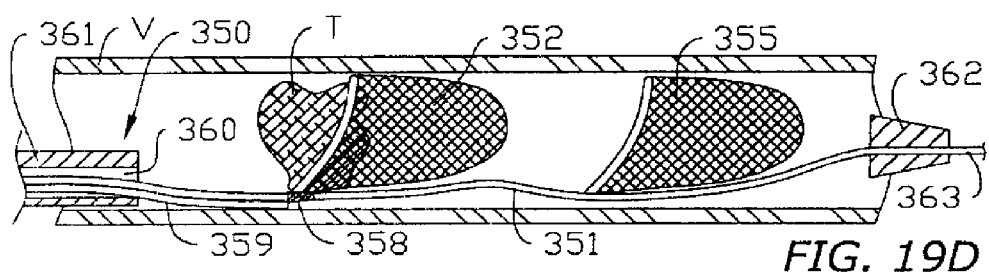

In FIG. 19D, once vascular device 350 is deployed in vessel V, thrombus T is removed in the following manner. Vascular filter support hoop 353 is rigidly attached to guide wire 351, while thrombectomy support hoop 353 is attached to pull wire 359 via ring 358. Thrombectomy element 352 then is refracted proximally to scrape along the wall of the vessel V by motion at the proximal end of pull wire 359. Thrombus T, located proximal to thrombectomy element 352, is excised so that it is captured in blood permeable sac 354 during the retraction.

Figure 19E:
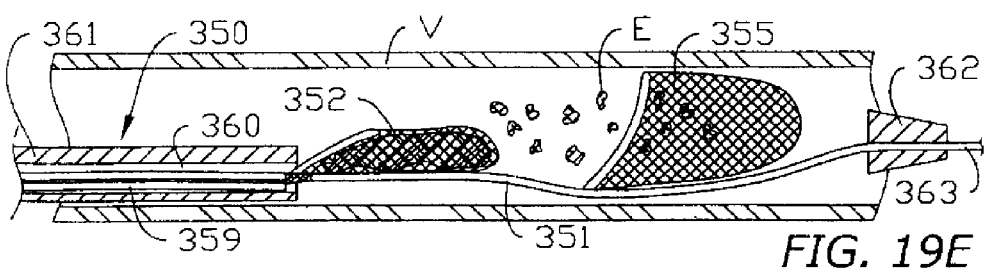

With respect to FIG. 19E, once thrombus T has been captured within sac 354, pull wire 359 is pulled proximally to cause the sides of thrombectomy support hoop 353 to collapse together to close the mouth of sac 354 (see FIG. 3). Additional proximal retraction of pull wire 359 causes support hoop 353 and sac 354 to enter within lumen 360 of delivery sheath 361, restoring normal blood flow to vessel V. Meanwhile, vascular filter 355 is in a position distal to thrombectomy element 352 to trap emboli E, i.e., pieces of plaque dislodged from either thrombus T or the walls of vessel V by thrombectomy element 352. Once any emboli E have been collected, filter hoop 356 and sac 357 are retracted into delivery sheath 361 by motion at the proximal end of guide wire 351, in a manner similar to the retraction of hoop 353 and sac 354. Once guide wire 351 has been fully retracted, and nose cone 362 at the distal end 363 of guide wire 351 is again in contact with delivery sheath 361, the delivery sheath is withdrawn with integrated vascular device 350, the trapped thrombus T, and any trapped emboli E.

As with previous embodiments, the compliant design of integrated vascular device 350 permits the device to be contracted to its delivery state within the guide wire lumen of conventional previously known interventional devices, thereby reducing time, effort, and trauma. The vascular device may be readily closed and retrieved upon completion of the interventional procedure.

Referring now to FIGS. 20A and 20B, an alternative embodiment of the integrated vascular device is described. Integrated vascular device 370 comprises guide wire 371, thrombectomy element 372, and vascular filter 373 having support hoop 374 and blood permeable sac 375. Filter hoop 374 is attached to guide wire 371, while thrombectomy element 372 is disposed to slide along guide wire 371. Alternatively, thrombectomy element 372 may be disposed on a separate catheter element that extends either through lumen 377 of delivery sheath 378 or is separately disposed proximal to vascular filter 373. FIG. 20A shows thrombectomy element 372 and vascular filter 373 contracted in a delivery state within lumen 377 of delivery sheath 378. Delivery sheath 378 includes nose cone 379 affixed to distal region 380 of guide wire 371. In FIG. 20B, integrated vascular device 370 is shown in the deployed state.

Thrombectomy element 372 may comprise any of a family of known thrombectomy, atherectomy, or, alternatively, drug delivery devices suitable for use in conjunction with vascular filter 373. Thrombectomy element 372 may, for example, comprise any of: a rotary ablation device, such as described in U.S. Pat. No. 4,867,156 to Stack et al., U.S. Pat. No. 4,990,134 to Auth, and U.S. Pat. No. 5,314,407 to Auth et al.; an atherectomy technology, such as described in U.S. Pat. No. 5,181,920 to Mueller et al., and U.S. Pat. No. 5,074,841 to Ademovic et al.; or a balloon embolectomy technology, such as described in U.S. Pat. No. 3,923,065 to Nozick et al., U.S. Pat. No. 5,769,871 to Mers Kelly et al., U.S. Pat. No. 5,192,290 to Hilal, U.S. Pat. No. 5,112,347 to Taheri, and U.S. Pat. No. 4,030,503 to Clark III. All of the foregoing patents are incorporated herein by reference. Thrombectomy element 372 may alternatively comprise a wire loop or ring, such as described for the embodiment of FIGS. 18A and 18B, a laser ablation device, a chemical flushing system, etc.

Figure 21A:
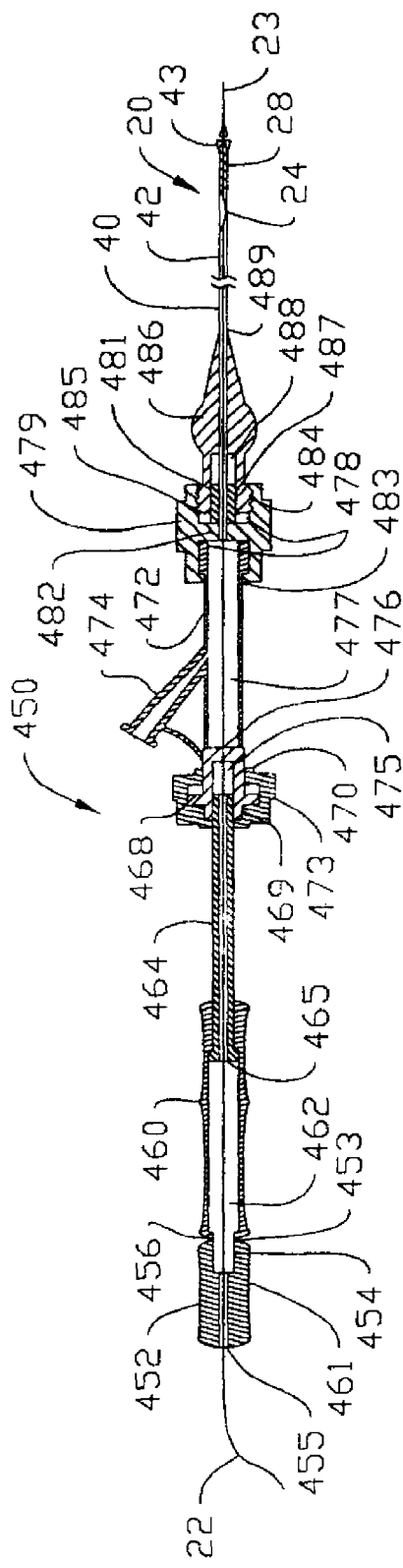
FIGS. 21A and 21B are side sectional views of a delivery system constructed in accordance with the present invention coupled to the vascular device of FIG. 5A, shown, respectively, in a delivery configuration and in a deployed configuration.
Figure 21B:
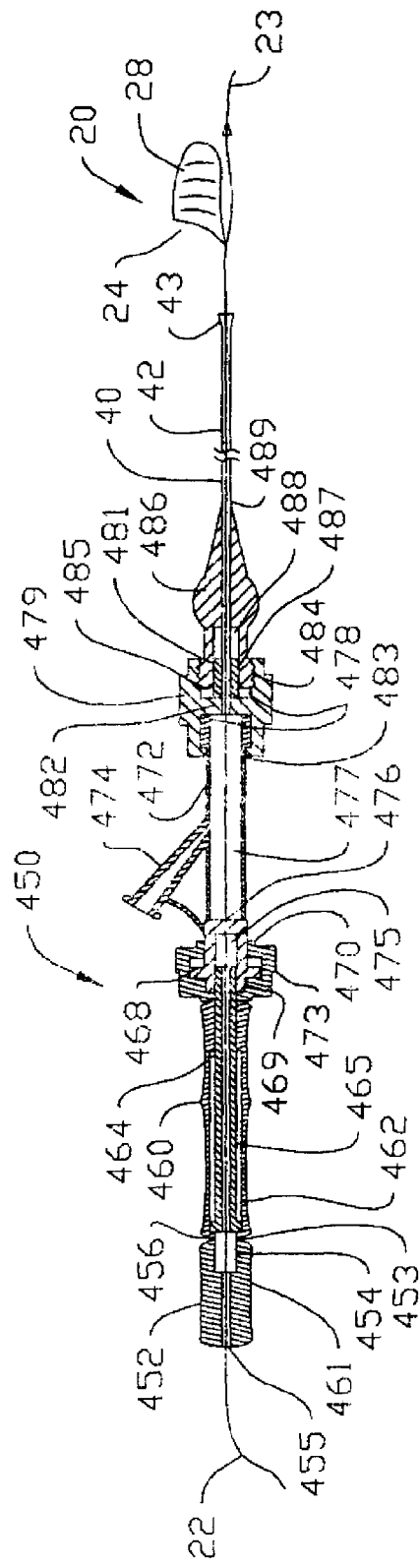

Referring now to FIGS. 21A and 21B, a delivery system configured for use with embodiments of the present invention is described. The delivery system facilitates deployment and retrieval of the embodiments by integrating the functions of a torquer, a Touhy Borst adapter, and a pusher into a single device. In FIG. 21, the delivery system is illustratively used in conjunction with vascular device 20 of FIGS. 2-5. In FIG.

21A, vascular device 20 is in the retracted delivery configuration, while in FIG. 21B vascular device 20 is in the expanded deployed configuration. Delivery system 450 comprises proximal screw cap 452, collet 456, handle 460, rod 464, central screw cap 468, lumen flushing section 472, distal hub 479, and nose piece 486.

Proximal screw cap 452 includes bore 453 with female screw thread 454 and guide wire lumen 455. Bore 453 extends proximally from the distal face of cap 452. Guide wire lumen 455 extends from the proximal end of bore 453 to the proximal end of cap 452.

Handle 460 comprises proximal male screw thread 461 configured to engage female screw thread 454 of cap 452, and lumen 462 configured to receive collet 456 in its proximal end and rod 464 in its distal end. Lumen 462 has a reduced diameter at the distal end of handle 460 that captures a step on the proximal end of rod 464. Thus, while collet 456 is removable received within lumen 462, rod 464 may translate and rotate within, but may not be removed from, lumen 462. Guide wire 422 freely passes through collet 456 when screw cap 452 is not securely fastened to handle 460. When cap 452 is securely fastened to handle 460, it causes collet 456 to elastically deform, decreasing the diameter of the lumen extending through the collet, and frictionally locking guide wire 422 into rigid attachment with collet 456. Guide wire 422 is thereby rigidly connected to handle 460.

Rod 464 further comprises guide wire lumen 465 extending therethrough. Rod 464 has its distal end rigidly and permanently affixed to central screw cap 468. Cap 468 comprises female screw thread 469 and lumen 470. Lumen 470 includes a proximal reduced-diameter step that captures rod 464 within the proximal end of cap 468, and a distal portion that receives lumen flushing or fluid port section 472.

Section 472 comprises male screw thread 473, side port 474, bore 475, guide wire lumen 476, and fluid lumen 477. Male screw thread 473 is configured to engage female thread 469 of cap 468. Section 472 includes a flange disposed just distal of thread 473 that is captured within lumen 470 of cap 468. Thus, cap 468 may be tightened onto and loosened from, but not removed from, section 472.

Rod 464 is received within bore 475 of section 472. Guide wire 22 passes between bore 475 and fluid lumen 477 within guide wire lumen 476. Fluid lumen 477 connects side port 474 to the guide wire lumen of delivery sheath 40. O-rings 478 provide a fluid seal at the distal end of lumen 477.

Distal hub 479 connects section 472 to nose piece 486. Hub 479 comprises bore 483, female screw thread 484, and annulus 485 containing tapered projection 481. Bore 483 includes flange 482 that rotatably receives section 472 in its proximal end. Nose piece 486 comprises male screw thread 487, tapered bore 488, and delivery sheath lumen 489. Male screw thread 487 is configured to engage female thread 484 in annulus 485 of hub 479. Tapered bore 488 allows tapered projection 481 of hub 479 to extend within nose piece 486 and permit delivery sheath 40 from delivery sheath lumen 489 to extend therethrough. O-rings 478 are disposed between the hub 479 and nose piece 486 and between hub 479 and section 472.

Delivery system 450 advantageously may be implemented in a variety of ways. For example, the delivery system may be offered with a delivery catheter or sheath pre-attached. In this embodiment, proximal screw cap 452 is loosened, and the proximal end of guide wire 22 may be passed through the delivery catheter or sheath, and delivery system 450, until vascular device 20 is in its retracted state within the delivery catheter or sheath. Insertion of the vascular device into the patient may then proceed. Alternatively, delivery system 450 may be commercially supplied in the configuration shown in FIG. 5A, i.e., pre-loaded with a delivery catheter or sheath, such as sheath 40, already attached and a vascular device, such as vascular device 20, retracted therein. As another alternative, delivery system 450 may be offered without either a delivery sheath or vascular device attached, or the delivery catheter or sheath may be an interventional instrument, such as an angioplasty, atherectomy, or stent delivery catheter.

Referring again to FIGS. 5A-5D in conjunction with FIGS. 21A and 21B, a method of using the delivery system of the present invention in conjunction with a vascular filter is described. With vascular device 20 contracted within distal end 42 of delivery sheath 40 (FIGS. 5A and 21A), delivery sheath 40 is attached to delivery system 450 by loosening proximal screw cap 452 and extending the proximal end of guide wire 22 through delivery system 450, with handle 460 in its proximal-most position (FIG. 21A). Screw cap 452 is then tightened to cause collet 456 to engage guide wire 22 to handle 460.

Delivery sheath 40 then is advanced through a patient's vasculature using well-known percutaneous techniques using distal end 23 of guide wire 22. If a vessel bifurcation is to be crossed during advancement, handle 460 may be rotated to divert the distal end of sheath 40 into the desired branch of the bifurcation. The rotational moment or torque applied to handle 460 is transmitted to guide wire 22 (when screw cap 452 is tightened), which causes distal end 23 to rotate and facilitates positioning of vascular device 20 in the proper side of the bifurcation. As shown in FIG. 5A, advancement continues until delivery sheath 40 is disposed at a desired location within a patient's vessel V, such as a coronary or carotid artery, as determined, for example, by the position of radiopaque band 43 under a fluoroscope.

With the vascular device in position, handle 460, and thus guide wire 22, is held stationary while section 472 and attached delivery sheath 40 are retracted proximally. Alternatively, handle 460 may be advanced while section 472 and sheath 40 are held stationary. In either case, when vascular device 20 is no longer confined within delivery sheath 40, support hoop 24 expands to seal against the walls of the vessel V, as depicted in FIGS. 5B and 21B. Blood continues to flow unimpeded through vessel V in direction A.

Depending on the medical procedure prescribed in conjunction with the use of vascular device 20, delivery sheath 40 may retrieve vascular device 20 at the conclusion of the procedure, or sheath 40 may be detached from delivery system 450 and removed from the patient. If sheath 40 is detached, guide wire 22 may be removed from delivery system 450 so that other interventional instruments, such as angioplasty catheters, atherectomy devices, or stent delivery systems may be advanced along guide wire 22 to position such devices at treatment zones located proximally of vascular device 20. Guide wire 22 and the interventional catheter then may be passed through and fastened to delivery system 450. For example, as shown in FIG. 5C, angioplasty balloon catheter 44 may be advanced along guide wire 22 to a position proximal of vascular device 20 so that device 20 may trap emboli E, i.e., pieces of plaque dislodged from the walls of vessel V by balloon 46.

Upon completion of the angioplasty procedure using angioplasty balloon catheter 44, handle 460 with attached guide wire 22 is pulled proximally to cause the sides of support hoop 24 to collapse together to close the mouth of sac 28 (FIG. 3). Additional proximal retraction of guide wire 22 causes support hoop 24 and sac 28 to enter at least partially within the guide wire lumen of angioplasty catheter 44. As depicted in FIG. 4D, only a portion of support hoop 24, near articulation region 26, and a distal portion of sac 28 extend out of the guide wire lumen of angioplasty catheter 44. Angioplasty catheter 44 then is withdrawn with vascular device 20 and any trapped emboli E.

It also may be beneficial during a medical procedure to introduce or withdraw fluids from the operative site. For example, it may be beneficial to deliver medicaments, or draw suction to remove blood. The delivery sheath lumen also may require flushing with saline to prevent clotting within the lumen. These and other procedures are made possible by side port 474 of section 472, which, as described hereinabove, is in fluid communication with the lumen of delivery sheath 40.

In addition to applications with vascular filters, delivery system 450 may be used as part of the thrombectomy/embolectomy procedure described herein above, as well as in a variety of other procedures.

Embodiments of the present invention may optionally be used in conjunction with a specially configured retrieval sheath. Applicant has determined that bunching of sac 28 in FIG. 5D may occur during retraction into catheter 44, resulting in a retrieval profile that may be difficult to navigate through a patient's vasculature. However, additional proximal retraction of guide wire 22 in an attempt to decrease the profile of sac 28 may generate stress loads sufficient to tear sac 28 and release captured emboli.

Figure 22A:
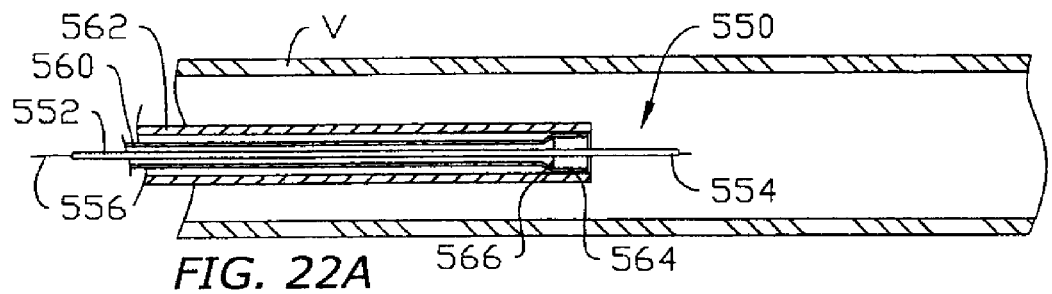
FIGS. 22A-22E are side sectional views depicting a method of deploying, using, and retrieving a vascular device of the present invention in conjunction with a specially configured retrieval sheath.

With reference to FIGS. 22A-22E, a specially configured retrieval sheath and methods of use with the vascular device of the present invention are described. As with FIG. 5, sizes have been exaggerated to illustrate structure. In FIG. 22A, guide wire 556 is positioned within vessel V using well-known percutaneous techniques. Vascular device 550 is disposed in its contracted delivery state within distal end 554 of delivery sheath 552. Retrieval sheath 560 and guide catheter 562 are advanced over delivery sheath 552 to a position located just proximal of distal end 554.

Retrieval sheath 560 includes collapsible flared end region 564, which is shown in a contracted delivery state within catheter 562 in FIG. 22A. Flared end region 564 has a deployed state, wherein the wall flares outward to form a frustrum of a cone, and a contracted state, wherein the wall is substantially cylindrical. Flared end region 564 preferably includes radiopaque band 566.

Figure 22B:
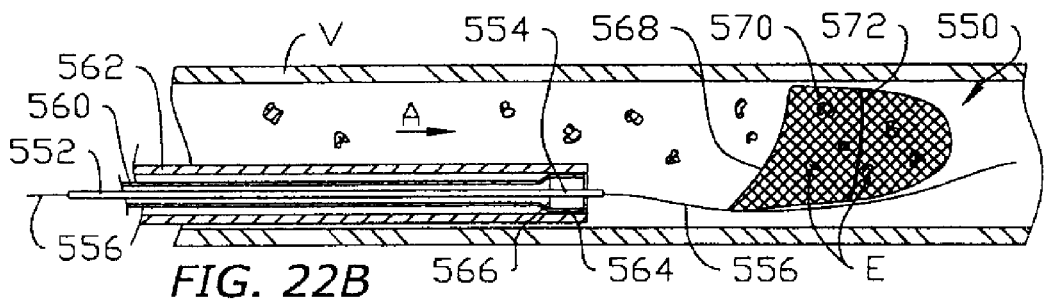

With respect to FIG. 22B, once delivery sheath 552 is disposed at a desired location within a patient's vessel V, guide wire 556 is held stationary while delivery sheath 552 is retracted proximally. Alternatively, delivery sheath 552 may be held stationary while guide wire 556 is advanced. In either case, when vascular device 550 is no longer confined within delivery sheath 552, support hoop 568 and attached blood permeable sac 570, expands to seal against the walls of the vessel V. Sac 570 further comprises radiopaque band 572. When in the deployed state, the curved regions of support hoop orient its articulation region concentrically against the inside wall of the vessel. Blood continues to flow unimpeded through vessel V in direction A.

With vascular device 550 deployed, an interventional procedure is performed proximal of the device. For example, guide catheter 562 may be an angioplasty balloon catheter similar to catheter 44 of FIGS. 5C and 5D. The interventional procedure generates emboli E proximal of device 550, which travel downstream and are captured in sac 570.

Figure 22C:
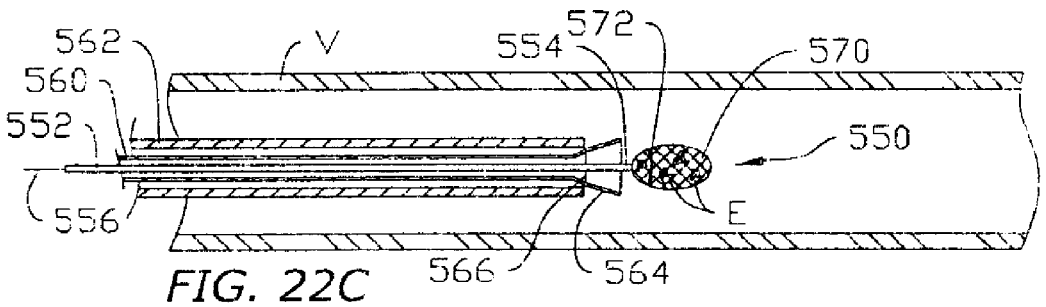

With respect to FIG. 22C, upon completion of the interventional procedure, guide wire 556 is pulled proximally to cause the sides of support hoop 568 to collapse together to close the mouth of sac 570 (see FIG. 3). Additional proximal retraction of guide wire 556 causes support hoop 568 and sac 570 to partially enter within distal end 554 of delivery sheath 552. If bunching of the sac is anticipated or suspected, flared sheath 560 may be advanced distally to expand end region 564, which comprises a suitable elastomeric material, such as latex, rubber, or a synthetic variant thereof.

Figure 22D:
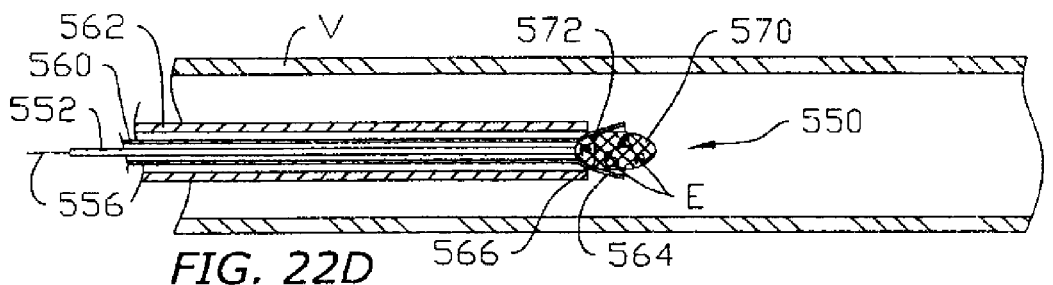
Figure 22E:
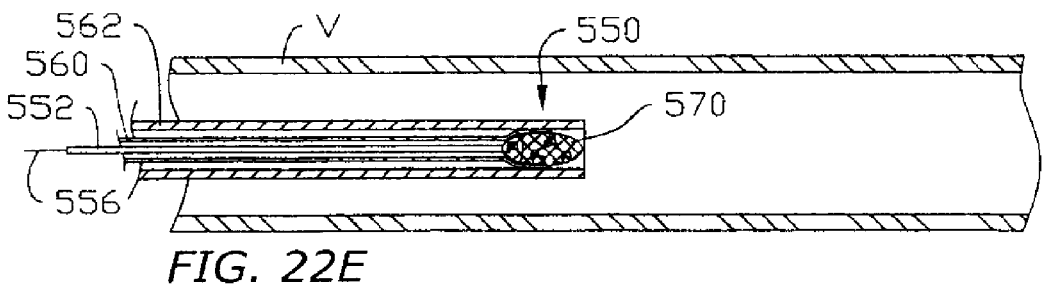

As depicted in FIG. 22D, delivery sheath 552 is retracted proximally while retrieval sheath 560 is held stationary, until radiopaque bands 572 and 566 are concentrically aligned, as determined, for example, with a fluoroscope. Then, as illustrated in FIG. 22E, sheaths 552 and 560 are simultaneously withdrawn proximally while guide catheter 562 is held stationary. This motion causes flared end region 564 to collapse sac 570 to its contracted state. In so doing, flared end region 564 applies a distributed load over the surface of sac 570, thereby decreasing the retrieval profile of sac 570 with reduced risk of rupture of sac 570.

Vascular device 550 also may be used in performing thrombectomy/embolectomy. In this case, vascular device 550 is advanced in its retracted state within delivery sheath 552 to a location distal of a lesion. Delivery sheath 552 is withdrawn proximally, and vascular device 550 is deployed. With support hoop 568 in contact with the vessel wall, vascular device 550 may be retracted proximally to scrape along the wall of the vessel and excise thrombus so that it is captured in sac 570. Delivery sheath 552, as well as flared sheath 560 and guide catheter 562, then may be reinserted into the vessel along guide wire 556, and vascular device 550 may be refracted and removed from the vessel in the manner described hereinabove.

With reference to FIGS. 23A and 23B, an alternative embodiment of the specially configured retrieval sheath, and methods of use with the vascular device of the present invention, are described. Again, sizes have been exaggerated to illustrate structure. In FIG. 23A, guide wire 582 has been positioned within vessel V using well-known percutaneous techniques. Vascular device 580 has been expanded to its deployed state after delivery within delivery sheath 584, in the manner discussed hereinabove. Support hoop 586 seals against the walls of vessel V, and blood permeable sac 588 is positioned to capture emboli E generated by, for example, an upstream interventional procedure. Blood continues to flow unimpeded through vessel V in direction A.

Delivery sheath 584 further comprises atraumatic expander 590 disposed on a distal end. Retrieval sheath 592 is advanced over delivery sheath 584 to a position located just proximal of expander 590. Retrieval sheath 592 includes expandable end region 594, which is shown in a contracted delivery state in FIG. 23A. Expandable end region 594 has a deployed state, wherein the wall flares outward to form a frustrum of a cone, and a contracted state, wherein the wall is substantially cylindrical. Expander 590 has a larger maximum diameter than end region 594. Expandable end region 594 preferably includes radiopaque band 596, while expander 590 preferably includes radiopaque band 598 so that their positions relative to one another may be accurately determined.

With respect to FIG. 23B, upon completion of the interventional procedure, guide wire 582 is pulled proximally to cause the sides of support hoop 586 to collapse together to close the mouth of sac 588 (see FIG. 3). Additional proximal retraction of guide wire 582 causes support hoop 586 and sac 588 to partially enter within the distal end of delivery sheath 584.

If bunching of the sac is anticipated or suspected, delivery sheath 584 may be retracted proximally while retrieval sheath 592 is held stationery to expand end region 594 of retrieval sheath 592 with expander 590. Delivery sheath 584 is retracted a sufficient distance to protect sac 588 and its embolic contents within end region 594. The distance may be determined by means of radiopaque bands 596 and 598. End region 594 comprises a suitable elastomeric material, such as latex, rubber or a synthetic variant thereof.

The profile of end region 594 in the expanded state allows for retraction of retrieval sheath 592, as well as delivery sheath 584 and vascular device 580 disposed therein, in a manner that mitigates dangerous interaction with the vascular wall. It also allows vascular device 580 to be retrieved in a partially collapsed state that reduces the risk of sac 588 tearing. As with vascular device 550, vascular device 580 may be used in performing thrombectomy/embolectomy.

The support hoops depicted herein illustratively are shown as oval or heart-shaped in the deployed state, where the shape is exaggerated for the sake of clarity. In preferred embodiments, the support hoops are substantially round when deployed, to ensure contact around the circumference of the support hoop and provide a positive seal against the arterial wall.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. An embolic protection filtering device, comprising:
   an elongate shaft having a proximal region, a distal region, and a longitudinal axis;
   a first filter affixed to the shaft adjacent the distal region, the first filter movable between a collapsed position and an expanded position;
   a second filter coupled to the shaft, the second filter movable between a collapsed position and an expanded position,
   wherein the first filter and the second filter in their respective expanded positions are disposed asymmetrically with respect to the longitudinal axis of the elongate shaft;
   a nose assembly having a proximal end and a distal end, the nose assembly affixed to the shaft adjacent to and distal of the distal-most filter;
   a delivery sheath slidably disposed over the elongate shaft, the delivery sheath having a first outer diameter, and
   wherein the nose assembly has a diameter which tapers distally from a first diameter substantially equal to the first outer diameter of the delivery sheath to a second lesser diameter.

2. The embolic protection filter device of claim 1, configured such that the first filter is movable between the collapsed and expanded positions independently of the movement of the second filter between the collapsed and expanded positions.

3. The embolic protection filter device of claim 2, wherein the first filter has a proximally disposed major opening.

4. The embolic protection filter device of claim 2, wherein the second filter has a proximally disposed major opening.

5. The embolic protection filter device of claim 1, wherein the first filter is substantially disposed to one side of the elongate shaft.

6. The embolic protection filter device of claim 1, wherein the second filter is substantially disposed to one side of the elongate shaft.

7. The embolic protection filter device of claim 1, wherein the first filter and the second filter are substantially disposed to one side of the elongate shaft.

8. An embolic protection filtering device, comprising:
   an elongate shaft having a proximal region and a distal region;
   a first filter affixed to the shaft adjacent the distal region, the first filter movable between a collapsed position and an expanded position;
   a second filter movable relative to the elongate shaft and movable between a collapsed position and an expanded position, the second filter including a fixedly attached ring slidably disposed over the elongate shaft;
   a nose assembly having a proximal end and a distal end, the nose assembly affixed to the shaft proximate to and distal of the distal-most filter;
   a delivery sheath slidably disposed over the elongate shaft and sized and adapted to contain the first filter and the second filter in their respective collapsed positions; and
   an element adapted to displace the ring longitudinally along the elongate shaft.

9. The embolic protection filter device of claim 8, configured such that the first filter is movable between the collapsed and expanded positions independently of the movement of the second filter between the collapsed and expanded positions.

10. The embolic protection filter device of claim 9, wherein the first filter has a proximally disposed major opening.

11. The embolic protection filter device of claim 9, wherein the second filter has a proximally disposed major opening.

12. The embolic protection filter device of claim 9, wherein the first filter is substantially disposed to one side of the elongate shaft.

13. The embolic protection filter device of claim 8, wherein the second filter is substantially disposed to one side of the elongate shaft.

* * * * *